(12) United States Patent
Fitzmaurice et al.

(10) Patent No.: US 6,656,726 B1
(45) Date of Patent: Dec. 2, 2003

(54) VIRAL EXPRESSION VECTORS

(75) Inventors: Wayne P. Fitzmaurice, Vacaville, CA (US); Gregory P. Pogue, Vacaville, CA (US); John A. Lindbo, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 0 days.

(21) Appl. No.: 09/565,616

(22) Filed: May 4, 2000

Related U.S. Application Data

(60) Provisional application No. 60/132,697, filed on May 4, 1999.

(51) Int. Cl.$^7$ .......................... C12N 15/00; C12N 5/00; C12N 5/04; C12N 15/82
(52) U.S. Cl. ................... 435/320.1; 435/410; 435/419; 435/468
(58) Field of Search .......................... 536/23.2, 23.72; 800/295, 278, 298, 317.3; 435/419, 468, 410, 414, 320.1

(56) References Cited

U.S. PATENT DOCUMENTS

| | | | |
|---|---|---|---|
| 5,316,931 A | 5/1994 | Donson et al. ........... | 435/172.3 |
| 5,405,783 A | 4/1995 | Pirrung et al. .............. | 436/518 |
| 5,412,087 A | 5/1995 | McGall et al. ............. | 536/24.3 |
| 5,445,934 A | 8/1995 | Fodor et al. .................... | 435/6 |
| 5,695,937 A | 12/1997 | Kinzler et al. ................. | 435/6 |
| 5,816,653 A | 10/1998 | Benson .................... | 297/284.4 |
| 5,866,785 A | 2/1999 | Donson et al. ............. | 800/205 |
| 5,889,190 A | 3/1999 | Donson et al. ............. | 800/288 |
| 5,889,191 A | 3/1999 | Turpen ....................... | 800/288 |
| 5,977,438 A | 11/1999 | Turpen et al. .............. | 800/288 |

FOREIGN PATENT DOCUMENTS

| | | |
|---|---|---|
| WO | WO 95/21248 | 10/1995 |
| WO | WO 00/66743 | 9/2000 |

OTHER PUBLICATIONS

Viaplana et al., Transient expression of a GUS reporter gene from cauliflower mosaic virus . . . , 2001, Journal of General Virology, vol. 82, pp. 59–65.*
Porta et al., Use of VIral Replicons for the Expression of Genes in Plants, 1996, Molecular Biotechnology, vol. 5, pp. 209–221.*
Ausubel, F.M., et al., Current Protocols in Molecular Biology—vol. 1 (1987).
Callis, J et al., "Introns increase gene expression in cultured maize cells," *Genes and Development,* 1:1183–1200 (1987).
Dawson, William and Krisi Lehto, "Regulation of Tobamovirus Gene Expression," *Advances in Virus Research* 38:307–342 (1991).
Donson, J., et al., "Agrobacterium–Mediated Infectivity of Cloned Digitaria Streak Virus DNA," *Virology* 162:248–250 (1988).

Epel, B., et al., "Plant virus movement protein dynamics probed with a GFP–protein fusion," Gene vol. 173(1):75–79 (1996).
Fraley, R., et al., "Expression of bacterial genes in plant cells," *Proc. Natl. Acad. Sci. U.S.A.,* 80:4803–4807 (1983).
Freshney, R.I., ed., *Animal Cell Culture: a practical approach* (1987) .
Fromm, M., et al., "Stable transformation of maize after gene transfer by electroporation," *Nature* 319:791–793 (1986).
Gardner, R., et al., "Potato spindle tuber viroid infections mediated by the Ti plasmid of *Agrobacterium tumefaciens,*" *Plant Mol. Biol.* 6:221–228 (1986).
Harlow, Ed and David Lane, eds., Antibodies, A Laboratory Manual, Cold Spring Harbor Laboratory (1988).
Lazarowitz, S., "Infectivity and complete nucleotide sequence of the genome of a South African isolate of maize streak virus," *Nucl. Acids Res.* 16(1):229–249 (1988).
Lewandowski, D and Willan O. Dawson., "Functions of the 126– and 183–kDA Proteins of Tobacco Mosaic Virus," *Virology* 271:90–98 (2000).
Matthews, R.E.F., *Plant Virology,* 3$^{rd}$ edition (1991).
McPherson, M.J., B.D. Hames and G.R. Taylor eds , the series *Methods in Enzymology* (Academic Press, Inc.): *PCR 2: A Practical Approach* (1995).
Potrykus, I., et al., "Molecular and general genetics of a hybrid foreign gene introduced into tobacco by direct gene transfer," *Mol. Gen. Genet.,* 199:169–177 (1985).
Sambrook, J. , E.F. Fritsch and T. Maniatis., *Molecular Cloning: A Laboratory Manual, 2$^{nd}$ edition,* Cold Spring Harbor Laboratory Press (1989).
Sanford, J.C. et al., "Optimizing the Biolistic Process for Different Biological Applications," *Methods in Enzymology,* 217:483–509 (1993).
Sijen, T., et al., "RNA–mediated virus resistance: Role of repeated transgenes and delineation of targeted regions," The Plant Cell, vol. 8(12): 227–2294 (1996).
Zhou, Guang–Yu., et al., "Introduction of Exogenous DNA into Cotton Embryos," Methods in Enzymology, 101:433–481 (1983).
"Methods for Plant Molecular Biology," A. Weissbach and H. Weissbach, eds., Academic Press, Inc., San Diego, Calif. (1988).

* cited by examiner

*Primary Examiner*—Deborah Crouch
*Assistant Examiner*—Joseph Woitach
(74) *Attorney, Agent, or Firm*—John C. Robbins; Thomas Gallegos; Quine Intellectual Property Law Group, P.C.

(57) ABSTRACT

The present invention provides nucleic acid sequences having an altered viral movement protein and 126/183 kDa replicase proteins further characterized in its ability to stabilize a transgene contained in a virus that expresses the altered movement protein. The present invention also provides viral vectors expressing the altered movement protein, cells transformed with the vectors, and host plants infected by the viral vectors.

14 Claims, 17 Drawing Sheets

Comparison of sequences from BSG1037 (SEQ ID NO.:3) and BSG1057 (SEQ ID
NO.:4) in the 30kDa movement protein coding region (nts 4903-5709).
Non-identities are indicated by _ and identities are indicated by *.

```
1037      ATGGCTCTAGTTGTTAAAGGAAAAGTGAATATCAATGAGTTTATCGACCT
1057      ATGGCTCTAGTTGTTAAAGGAAAAGTGAATATCAATGAGTTTATCGACCT
          **************************************************

1037      GACAAAAATGGAGAAGATCTTACCGTCGATGTTTACCCCTGTAAAGAGTG
1057      GACAAAAATGGAGAAGATCTTACCGTCGATGTTTACCCCTGTAAAGAGTG
          **************************************************

1037      TTATGTGTTCCAAAGTTGATAAAATAATGGTTCATGAGAATGAGTCATTG
1057      TTATGTGTTCCAAAGTTGATAAAATAATGGTTCATGAGAATGAGTCATTG
          **************************************************

1037      TCAGGGGTGAACCTTCTTAAAGGAGTTAAGCTTATTGATAGTGGATACGT
1057      TCAGGGGTGAACCTTCTTAAAGGAGTTAAGCTTATTGATAGTGGATACGT
          **************************************************

1031      CTGTTTAGCCGGTTTGGTCGTCACGGGCGAGTGGAACTTGCCTGACAATT
1057      CTGTTTAGCCGGTTTGGTCGTCACGGGCGAGTGGAACTTGCCTGACAATT
          **************************************************

1037      GCAGAGGAGGTGTGAGCGTGTGTCTGGTGGACAAAAGGATGGAAAGAGCC
1057      GCAGAGGAGGTGTGAGCGTGTGTCTGGTGGACAAAAGGATGGAAAGAGCC
          **************************************************

1037      GACGAGGCCACTCTCGGATCTTACTACACAGCAGCTGCAAAGAAAAGATT
1057      GACGAGGCCATTCTCGGATCTTACTACACAGCAGCTGCAAAGAAAAGATT
          ********* ****************************************
                   _

1037      TCAGTTCAAGGTCGTTCCCAATTATGCTATAACCACCCAGGACGCGATGA
1057      TCAGTTCAAGGTCGTTCCCAATTATGCTATAACCACCCAGGACGCGATGA
          **************************************************

1037      AAAACGTCTGGCAAGTTTTAGTTAATATTAGAAATGTGAAGATGTCAGCG
1051      GAAACGTCTGGCAAGTTTTAGTTAATATTAGAAATGTGAAGATGTCAGCG
           *************************************************
          _

1037      GGTTTCTGTCCGCTTTCTCTGGAGTTTGTGTCGGTGTGTATTGTTTATAG
1057      GGTTTCTGTCCGCTTTCTCTGGAGTTTGTGTCGGTGTGTATTGTTTATAG
          **************************************************

1037      AAATAATATAAAATTAGGTTTGAGAGAGAAGATTACAAACGTGAGAGACG
1057      AAATAATATAAAATTAGGTTTGAGAGAGAAGATTACAAACGTGAGAGACG
          **************************************************

1037      GAGGGCCCATGGAACTTACAGAAGAAGTCGTTGATGAGTTCATGGAAGAT
1057      GAGGGCCCATGGAACTTACAGAAGAAGTCGTTGATGAGTTCATGGAAGAT
          **************************************************

1037      GTCCCTATGTCGATCAGGCTTGCAAAGTTTCGATCTCGAACCGGAAAAAA
1057      GTCCCTATGTCGATCAGGCTTGCAAAGTTTCGATCTCGAACCGGAAAAAA
          **************************************************
```

Figure 1a

```
1037    GAGTGATGTCCGCAAAGGGAAAAATAGTAGTAGTGATCGGTCAGTGCCGA
1057    GAGTGATGTCCGCAAAGGGAAAAATAGTAGTAGTGATCGGTCAGTGCCGA
        **************************************************

1037    ACAAGAACTATAGAAATGTTAAGGATTTTGGAGGAATGAGTTTTAAAAAG
1057    ACAAGAACTATAGAAATGTTAAGGATTTTGGAGGAATGAGTTTTAAAAAG
        **************************************************

1037    AATAATTTAATCGATGATGATTCGGAGGCTACTGTCGCCGAATCGGATTC
1057    AATAATTTAATCGATGATGATTCGGAGGCTACTGTCGCCGAATCGGATTC
        **************************************************

1037    GTTTTAA
1057    GTTTTAA
        *******
```

Figure 1b

**Comparison of sequences from BSG1037 (SEQ ID No.:5) and BSG1057 (SEQ ID NO.:6) in the 30kDa movement protein (aa1-268). Non-identities are indicated by _ and identities are indicated by *.**

```
1037  MALVVKGKVNINEFIDLTKMEKILPSMFTPVKSVMCSKVDKIMVHENESL
1057  MALVVKGKVNINEFIDLTKMEKILPSMFTPVKSVMCSKVDKIMVHENESL
      **************************************************

1037  SGVNLLKGVKLIDSGYVCLAGLVVTGEWNLPDNCRGGVSVCLVDKRMERA
1057  SGVNLLKGVKLIDSGYVCLAGLVVTGEWNLPDNCRGGVSVCLVDKRMERA
      **************************************************

1037  DEATLGSYYTAAAKKRFQFKVVPNYAITTQDAMKNVWQVLVNIRNVKMSA
1057  DEAILGSYYTAAAKKRFQFKVVPNYAITTQDAMRNVWQVLVNIRNVKMSA
      *** ***************************** ****************
         _                             _

1037  GFCPLSLEFVSVCIVYRNNIKLGLREKITNVRDGGPMELTEEVVDEFMED
1057  GFCPLSLEFVSVCIVYRNNIKLGLREKITNVRDGGPMELTEEVVDEFMED
      **************************************************

1037  VPMSIRLAKFRSRTGKKSDVRKGKNSSSDRSVPNKNYRNVKDFGGMSFKK
1057  VPMSIRLAKFRSRTGKKSDVRKGKNSSSDRSVPNKNYRNVKDFGGMSFKK
      **************************************************

1037  NNLIDDDSEATVAESDSF
1057  NNLIDDDSEATVAESDSF
      ******************
```

Figure 2

BSG1037 -> Graphic Map

DNA sequence   10403 b.p.   GTATTTTTACAA ... CGACTCACTATA   circular

126/183 reading frame begins at 69, 3417 is suppressible stop codon, and ends at 4919.30K BSG1037 -> Graphic Map DNA sequence 10403 b.p. GTATTTTTACAA ... CGACTCACTATA circular

Complete sequence of BSG 1037 (SEQ ID NO.: 1)

GTATTTTTACAACAATTACCAACAACAACAAACAACAGACAACATTACAATTACT
ATTTACAATTACAATGGCATACACA
CAGACAGCTACCACATCAGCTTTGCTGGACACTGTCCGAGGAAACAACTCCTTGG
TCAATGATCTAGCAAAGCGTCGTCT
TTACGACACAGCGGTTGAAGAGTTTAACGCTCGTGACCGCAGGCCCAAGGTGAA
CTTTTCAAAAGTAATAAGCGAGGAGC
AGACGCTTATTGCTACCCGGGCGTATCCAGAATTCCAAATTACATTTTATAACAC
GCAAAATGCCGTGCATTCGCTTGCA
GGTGGATTGCGATCTTTAgAACTGGAATATCTGATGATGCAAATTCCCTACGGAT
CATTGACTTATGACATAGGCGGGAA
TTTTGCATCGCATCTGTTCAAGGGACGAGCATATGTACACTGCTGCATGCCCAAC
CTGGACGTTCGAGACATCATGCGGC
ACGAAGGCCAGAAAGACAGTATTGAACTATACCTTTCTAGGCTAGAGAGAGGGG
GGAAAACAGTCCCCAACTTCCAAAAG
GAAGCATTTGACAGATACGCAGAAATTCCTGAAGACGCTGTCTGTCACAATACTT
TCCAGACATGCGAACATCAGCCGAT
GCAGCAATCAGGCAGAGTGTATGCCATTGCGCTACACAGCATATATGACATACCA
GCCGATGAGTTCGGGGCGGCACTCT
TGAGGAAAAATGTCCATACGTGCTATGCCGCTTTCCACTTCTCCGAGAACCTGCT
TCTTGAAGATTCATGCGTCAATTTG
GACGAAATCAACGCGTGTTTTCGCGCGATGGAGACAAGTTGACCTTTTCTTTTG
CATCAGAGAGTACTCTTAATTACTG
TCATAGTTATTCTAATATTCTTAAGTATGTGTGCAAAACTTACTTCCCGGCCTCTA
ATAGAGAGGTTTACATGAAGGAGT
TTTTAGTCACCAGAGTTAATACCTGGTTTTGTAAGTTTTCTAGAATAGATACTTTT
CTTTTGTACAAAGGTGTGGCCCAT
AAAAGTGTAGATAGTGAGCAGTTTTATACTGCAATGGAAGACGCATGGCATTAC
AAAAAGACTCTTGCAATGTGCAACAG
CGAGAGAATCCTCCTTGAGGATTCATCATCAGTCAATTACTGGTTTCCCAAAATG
AGGGATATGGTCATCGTACCATTAT
TCGACATTTCTTTGGAGACTAGTAAGAGGACGCGCAAGGAAGTCTTAGTGTCCAA
GGATTTCGTGTTTACAGTGCTTAAC
CACATTCGAACATACCAGGCGAAAGCTCTTACATACGCAAATGTTTTGTCCTTCG
TCGAATCGATTCGATCGAGGGTAAT
CATTAACGGTGTGACAGCGAGGTCCGAATGGGATGTGGACAAATCTTTGTTACAA
TCCTTGTCCATGACGTTTTACCTGC
ATACTAAGCTTGCCGTTCTAAAGGATGACTTACTGATTAGCAAGTTTAGTCTCGG
TTCGAAAACGGTGTGCCAGCATGTG
TGGGATGAGATTTCGCTGGCGTTTGGGAACGCATTTCCCTCCGTGAAAGAGAGGC
TCTTGAACAGGAAACTTATCAGAGT
GGCAGGCGACGCATTAGAGATCAGGGTGCCTGATCTATATGTGACCTTCCACGAC
AGATTAGTGACTGAGTACAAGGCCT
CTGTGGACATGCCTGCGCTTGACATTAGGAAGAAGATGGAAGAAACGGAAGTGA
TGTACAATGCACTTTCAGAATTATCG
GTGTTAAGGGAGTCTGACAAATTCGATGTTGATGTTTTTCCCAGATGTGCCAAT
CTTTGGAAGTTGACCCAATGACGGC

Figure 5a

AGCGAAGGTTATAGTCGCGGTCATGAGCAATGAGAGCGGTCTGACTCTCACATTT
GAACGACCTACTGAGGCGAATGTTG
CGCTAGCTTTACAGGATCAAGAGAAGGCTTCAGAAGGTGCATTGGTAGTTACCTC
AAGAGAAGTTGAAGAACCGTCCATG
AAGGGTTCGATGGCCAGAGGAGAGTTACAATTAGCTGGTCTTGCTGGAGATCATC
CGGAATCGTCCTATTCTAAGAACGA
GGAGATAGAGTCTTTAGAGCAGTTTCATATGGCGACGGCAGATTCGTTAATTCGT
AAGCAGATGAGCTCGATTGTGTACA
CGGGTCCGATTAAAGTTCAGCAAATGAAAACTTTATCGATAGCCTGGTAGCATC
ACTATCTGCTGCGGTGTCAATCTC
GTCAAGATCCTCAAAGATACAGCTGCTATTGACCTTGAAACCCGTCAAAAGTTTG
GAGTCTTGGATGTTGCATCTAGGAA
GTGGTTAATCAAACCAACGGCCAAGAGTCATGCATGGGGTGTTGTTGAAACCCAC
GCGAGGAAGTATCATGTGGCGCTTT
TGGAATATGATGAGCAGGGTGTGGTGACATGCGATGATTGGAGAAGAGTAGCTG
TTAGCTCTGAGTCTGTTGTTTATTCC
GACATGGCGAAACTCAGAACTCTGCGCAGACTGCTTCGAAACGGAGAACCGCAT
GTCAGTAGCGCAAAGGTTGTTCTTGT
GGACGGAGTTCCGGGCTGTGGAAAAACCAAAGAAATTCTTTCCAGGGTTAATTTT
GATGAAGATCTAATTTTAGTACCTG
GGAAGCAAGCCGCGGAAATGATCAGAAGACGTGCGAATTCCTCAGGGATTATTG
TGGCCACGAAGGACAACGTTAAAACC
GTTGATTCTTTCATGATGAATTTTGGGAAAAGCACACGCTGTCAGTTCAAGAGGT
TATTCATTGATGAAGGGTTGATGTT
GCATACTGGTTGTGTTAATTTTCTTGTGGCGATGTCATTGTGCGAAATTGCATATG
TTTACGGAGACACACAGCAGATTC
CATACATCAATAGAGTTTCAGGATTCCCGTACCCCGCCCATTTTGCCAAATTGGA
AGTTGACGAGGTGGAGACACGCAGA
ACTACTCTCCGTTGTCCAGCCGATGTCACACATTATCTGAACAGGAGATATGAGG
GCTTTGTCATGAGCACTTCTTCGGT
TAAAAGTCTGTTTCGCAGGAGATGGTCGGCGGAGCCgCCGTGATCAATCCGATC
TCAAAACCCTTGCATGGCAAGATCT
TGACTTTTACCCAATCGGATAAAGAAGCTCTGCTTTCAAGAGGGTATTCAGATGT
TCACACTGTGCATGAAGTGCAAGGC
GAGACATACTCTGATGTTTCACTAGTTAGGTTAACCCCTACACCGGTCTCCATCAT
TGCAGGAGACAGCCCACATGTTTT
GGTCGCATTGTCAAGGCACACCTGTTCGCTCAAGTACTACACTGTTGTTATGGAT
CCTTTAGTTAGTATCATTAGAGATC
TAGAGAAACTTAGCTCGTACTTGTTAGATATGTATAAGGTCGATGCAGGAACACA
ATAGCAATTACAGATTGACTCGGTG
TTCAAAGGTTCCAATCTTTTGTTGCAGCGCCAAAGACTGGTGATATTTCTGATAT
GCAGTTTTACTATGATAAGTGTCT
CCCAGGCAACAGCACCATGATGAATAATTTTGATGCTGTTACCATGAGGTTGACT
GACATTTCATTGAATGTCAAAGATT
GCATATTGGATATGTCTAAGTCTGTTGCTGCGCCTAAGGATCAAATCAAACCACT
AATACCTATGGTACGAACGGCGGCA
GAAATGCCACGCCAGACTGGACTATTGGAAAATTTAGTGGCGATGATTAAAAGA
AACTTTAACGCACCCGAGTTGTCTGG

Figure 5b

```
CATCATTGATATTGAAAATACTGCATCTTTGGTTGTAGATAAGTTTTTTGATAGTT
ATTTGCTTAAAGAAAAAAGAAAAC
CAAATAAAAATGTTTCTTTGTTCAGTAGAGAGTCTCTCAATAGATGGTTAGAAAA
GCAGGAACAGGTAACAATAGGCCAG
CTCGCAGATTTTGATTTTGTGGATTTGCCAGCAGTTGATCAGTACAGACACATGA
TTAAAGCACAACCCAAACAAAAGTT
GGACACTTCAATCCAAACGGAGTACCCGGCTTTGCAGACGATTGTGTACCATTCA
AAAAGATCAATGCAATATTCGGCC
CGTTGTTTAGTGAGCTTACTAGGCAATTACTGGACAGTGTTGATTCGAGCAGATT
TTTGTTTTTCACAAGAAAGACACCA
GCGCAGATTGAGGATTTCTTCGGAGATCTCGACAGTCATGTGCCGATGGATGTCT
TGGAGCTGGATATATCAAAATACGA
CAAATCTCAGAATGAATTCCACTGTGCAGTAGAATACGAGATCTGGCGAAGATTG
GGTTTCGAAGACTTCTTGGGAGAAG
TTTGGAAACAAGGGCATAGAAAGACCACCCTCAAGGATTATACCGCAGGTATAA
AAACTTGCATCTGGTATCAAAGAAAG
AGCGGGGACGTCACGACGTTCATTGGAAACACTGTGATCATTGCTGCATGTTTGG
CCTCGATGCTTCCGATGGAGAAAAT
AATCAAAGGAGCCTTTTGCGGTGACGATAGTCTGCTGTACTTTCCAAAGGGTTGT
GAGTTTCCGGATGTGCAACACTCCG
CGAATCTTATGTGGAATTTTGAAGCAAAACTGTTTAAAAAACAGTATGGATACTT
TTGCGGAAGATATGTAATACATCAC
GACAGAGGATGCATTGTGTATTACGATCCCCTAAAGTTGATCTCGAAACTTGGTG
CTAAACACATCAAGGATTGGGAACA
CTTGGAGGAGTTCAGAAGGTCTCTTTGTGATGTTGCTGTTTCGTTGAACAATTGTG
CGTATTACACACAGTTGGACGACG
CTGTATGGGAGGTTCATAAGACCGCCCCTCCAGGTTCGTTTGTTTATAAAAGTCT
GGTGAAGTATTTGTCTGATAAAGTT
CTTTTTAGAAGTTTGTTTATAGATGGCTCTAGTTGTTAAAGGAAAAGTGAATATC
AATGAGTTTATCGACCTGACAAAAA
TGGAGAAGATCTTACCGTCGATGTTTACCCCTGTAAAGAGTGTTATGTGTTCCAA
AGTTGATAAAATAATGGTTCATGAG
AATGAGTCATTGTCAGGGGTGAACCTTCTTAAAGGAGTTAAGCTTATTGATAGTG
GATACGTCTGTTTAGCCGGTTTGGT
CGTCACGGGCGAGTGGAACTTGCCTGACAATTGCAGAGGAGGTGTGAGCGTGTG
TCTGGTGGACAAAAGGATGGAAAGAG
CCGACGAGGCCACTCTCGGATCTTACTACACAGCAGCTGCAAAGAAAAGATTTCA
GTTCAAGGTCGTTCCCAATTATGCT
ATAACCACCCAGGACGCGATGAAAAACGTCTGGCAAGTTTTAGTTAATATTAGAA
ATGTGAAGATGTCAGCGGGTTTCTG
TCCGCTTTCTCTGGAGTTTGTGTCGGTGTGTATTGTTTATAGAAATAATATAAAT
TAGGTTTGAGAGAGAAGATTACAA
ACGTGAGAGACGGAGGGCCCATGGAACTTACAGAAGAAGTCGTTGATGAGTTCA
TGGAAGATGTCCCTATGTCGATCAGG
CTTGCAAAGTTTCGATCTCGAACCGGAAAAAGAGTGATGTCCGCAAAGGGAAA
AATAGTAGTAGTGATCGGTCAGTGCC
GAACAAGAACTATAGAAATGTTAAGGATTTTGGAGGAATGAGTTTTAAAAAGAA
TAATTTAATCGATGATGATTCGGAGG
```

Figure 5c

CTACTGTCGCCGAATCGGATTCGTTTTAAATAGATCTTACAGTATCACTACTCCAT
CTCAGTTCGTGTTCTTGTCATTAA
TTAAATGGCTAGCAAAGGAGAAGAACTTTTCACTGGAGTTGTCCCAATTCTTGTT
GAATTAGATGGTGATGTTAATGGGC
ACAAATTTTCTGTCAGTGGAGAGGGTGAAGGTGATGCTACATACGGAAAGCTTAC
CCTTAAATTTATTTGCACTACTGGA
AAACTACCTGTTCCATGGCCAACACTTGTCACTACTTTCTCTTATGGTGTTCAATG
CTTTTCCCGTTATCCGGATCATAT
GAAACGGCATGACTTTTCAAGAGTGCCATGCCCGAAGGTTATGTACAGGAACGC
ACTATATCTTTCAAAGATGACGGGA
ACTACAAGACGCGTGCTGAAGTCAAGTTTGAAGGTGATACCCTTGTTAATCGTAT
CGAGTTAAAAGGTATTGATTTTAAA
GAAGATGGAAACATTCTCGGACACAAACTCGAGTACAACTATAACTCACACAAT
GTATACATCACGGCAGACAAACAAAA
GAATGGAATCAAAGCTAACTTCAAAATTCGCCACAACATTGAAGATGGATCCGTT
CAACTAGCAGACCATTATCAACAAA
ATACTCCAATTGGCGATGGCCCTGTCCTTTTACCAGACAACCATTACCTGTCGAC
ACAATCTGCCCTTTCGAAAGATCCC
AACGAAAAGCGTGACCACATGGGCCTTCTTGAGTTTGTAACTGCTGCTGGGATTA
CACATGGCATGGATGAGCTCTACAA
ATAATGACACTCGAGGGGTAGTCAAGATGCATAATAAATAACGGATTGTGTCCGT
AATCACACGTGGTGCGTACGATAAC
GCATAGTGTTTTCCCTCCACTTAAATCGAAGGGTTGTGTCTTGGATCGCGCGGGT
CAAATGTATATGGTTCATATACAT
CCGCAGGCACGTAATAAAGCGAGGGGTTCGGGTCGAGGTCGGCTGTGAAACTCG
AAAAGGTTCCGGAAAACAAAAAAGAG
AGTGGTAGGTAATAGTGTTAATAATAAGAAAATAAATAATAGTGGTAAGAAAGG
TTTGAAAGTTGAGGAAATTGAGGATA
ATGTAAGTGATGACGAGTCTATCGCGTCATCGAGTACGTTTTAATCAATATGCCT
TATACAATCAACTCTCCGAGCCAAT
TTGTTTACTTAAGTTCCGCTTATGCAGATCCTGTGCAGCTGATCAATCTGTGTACA
AATGCATTGGGTAACCAGTTTCAA
ACGCAACAAGCTAGGACAACAGTCCAACAGCAATTTGCGGATGCCTGGAAACCT
GTGCCTAGTATGACAGTGAGATTTCC
TGCATCGGATTTCTATGTGTATAGATATAATTCGACGCTTGATCCGTTGATCACGG
CGTTATTAAATAGCTTCGATACTA
GAAATAGAATAATAGAGGTTGATAATCAACCCGCACCGAATACTACTGAAATCG
TTAACGCGACTCAGAGGGTAGACGAT
GCGACTGTAGCTATAAGGGCTTCAATCAATAATTTGGCTAATGAACTGGTTCGTG
GAACTGGCATGTTCAATCAAGCAAG
CTTTGAGACTGCTAGTGGACTTGTCTGGACCACAACTCCGGCTACTTAGCTATTGT
TGTGAGATTTCCTAAAATAAAGTC
ACTGAAGACTTAAAATTCAGGGTGGCTGATACCAAAATCAGCAGTGGTTGTTCGT
CCACTTAAATATAACGATTGTCATA
TCTGGATCCAACAGTTAAACCATGTGATGGTGTATACTGTGGTATGGCGTAAAAC
AACGGAAAAGTCGCTGAAGACTTAA
AATTCAGGGTGGCTGATACCAAAATCAGCAGTGGTTGTTCGTCCACTTAAAAATA
ACGATTGTCATATCTGGATCCAACA

Figure 5d

GTTAAACCATGTGATGGTGTATACTGTGGTATGGCGTAAACAACGGAGAGGTTCG
AATCCTCCCCTAACCGCGGgtagcg
gccca

Figure 5e

Complete Sequence of BSG 1057 (SEQ ID NO.: 2):

```
GTATTTTTACAACAATTACCAACAACAACAAACAACAGACAACATTACAATT
ACTATTTACAATTACAATGGCATACACA
CAGACAGCTACCACATCAGCTTTGCTGGACACTGTCCGAGGAAACAACTCCT
TGGTCAATGATCTAGCAAAGCGTCGTCT
TTACGACACAGCGGTTGAAGAGTTTAACGCTCGTGACCGCAGGCCCAAGGTG
AACTTTTCAAAAGTAATAAGCGAGGAGC
AGACGCTTATTGCTACCCGGGCGTATCCAGAATTCCAAATTACATTTTATAAC
ACGCAAAATGCCGTGCATTCGCTTGCA
GGTGGATTGCGATCTTTAGAACTGGAATATCTGATGATGCAAATTCCCTACGG
ATCATTGACTTATGACATAGGCGGGAA
TTTTGCATCGCATCTGTTCAAGGGACGAGCATATGTACACTGCTGCATGCCCA
ACCTGGACGTTCGAGACATCATGCGGC
ACGAAGGCCAGAAAGACAGTATTGAACTATACCTTTCTAGGCTAGAGAGAGG
GGGGAAAACAGTCCCCAACTTCCAAAAG
GAAGCATTTGACAGATACGCAGAAATTCCTGAAGACGCTGTCTGTCACAATA
CTTTCCAGACATGCAACATCAGCCGAT
GCAGCAATCAGGCAGAGTGTATGCCATTGCGCTACACAGCATATATGACATA
CCAGCCGATGAGTTCGGGGCGGCACTCT
TGAGGAAAAATGTCCATACGTGCTATGCCGCTTTCCACTTCTCCGAGAACCTG
CTTCTTGAAGATTCATGCGTCAATTTG
GACGAAATCAACGCGTGTTTTCGCGCGATGGAGACAAGTTGACCTTTTCTTT
TGCATCAGAGAGTACTCTTAATTACTG
TCATAGTTATTCTAATATTCTTAAGTATGTGTGCAAAACTTACTTCCCGGCCTC
TAATAGAGAGGTTTACATGAAGGAGT
TTTTAGTCACCAGAGTTAATACCTGGTTTTGTAAGTTTTCTAGAATAGATACTT
TTCTTTTGTACAAAGGTGTGGCCCAT
AAAAGTGTAGATAGTGAGCAGTTTTATACTGCAATGGAAGACGCATGGCATT
ACAAAAAGACTCTTGCAATGTGCAACAG
CGAGAGAATCCTCCTTGGGGATTCATCATCAGTCAATTACTGGTTTCCCAAAA
TGAGGGATATGGTCATCGTACCATTAT
TCGACATTTCTTTGGAGACTAGTAAGAGGACGCGCAAGGAAGTCTTAGTGTC
CAAGGATTTCGTGTTCACAGTGCTTAAC
CACATTCGAACATACCAGGCGAAAGCTCTTACATACGCAAATGTTTTGTCCTT
CGTCGAATCGATTCGATCGAGGGTAAT
CATTAACGGTGTGACAGCGAGGTCCGAATGGGATGTGGACAAATCTTTGTTA
CAATCCTTGTCCATGACGTTTTACCTGC
ATACTAAGCTTGCCGTTCTAAAGGATGACTTACTGATTAGCAAGTTTAGTCTC
GGTTCGAAAACGGTGTGCCAGCATGTG
TGGGATGAGATTTCGCTGGCGTTTGGGAACGCATTTCCCTCCGTGAAAGAGA
GGCTCTTAACAGGAAACTTATCAGAGT
GGCAGGCGACGCATTAGAGATCAGGGTGCCTGATCTATATGTGACCTTCCAC
GACAGATTAGTGACTGAGTACAAGGCCT
CTGTGGACATGCCTGCGCTTGACATTAGGAAGAAGATGGAAGAAACGGAAGT
GATGTACAATGCACTTTCAGAATTATCG
```

Figure 6a

```
GTGTTAAGGGAGTCTGACAAATTCGATGTTGATGTTTTTCCCAGATGTGCCA
ATCTTTGGAAGTTGACCCAATGACGGC
AGCGAAGGTTATAGTCGCGGTCATGAGCAATGAGAGCGGTCTGACTCTCACA
TTTGAACGACCTACTGAGGCGAATGTTG
CGCTAGCTTTACAGGATCAAGAGAAGGCTTCAGAAGGTGCATTGGTAGTTAC
CTCAAGAGAAGTTGAAGAACCGTCCATG
AAGGGTTCGATGGCCAGAGGAGAGTTACAATTAGCTGGTCTTGCTGGAGATC
ATCCGGAATCGTCCTATTCTAAGAACGA
GGAGATAGAGTCTTTAGAGCAGTTTCATATGGCGACGGCAGATTCGTTAATTC
GTAAGCAGATGAGCTCGATTGTGTACA
CGGGTCCGATTAAAGTTCAGCAAATGAAAAACTTTATCGATAGCCTGGTAGC
ATCACTATCTGCTGCGGTGTCGAATCTC
GTCAAGATCCTCAAAGATACAGCTGCTATTGACCTTGAAACCCGTCAAAAGT
TTGGAGTCTTGGATGTTGCATCTAGGAA
GTGGTTAATCAAACCAACGGCCAAGAGTCATGCATGGGGTGTTGTTGAAACC
CACGCGAGGGAGTATCATGTGGCGCTTT
TGGAATATGATGAGCAGGGTGTGGTGACATGCGATGATTGGAGAAGAGTAGC
TGTTAGCTCTGAGTCTGTTGTTTATTCC
GACATGGCGAAACTCAGAACTCTGCGCAGACTGCTTCGAAACGGAGAACCGC
ATGTCAGTAGCGCAAAGGTTGTTCTTGT
GGACGGAGTTCCGGGCTGTGGAAAAACCAAAGAAATTCTTTCCAGGGTTAAT
TTTGATGAAGATCTAATTTTAGTACCTG
GGAAGCAAGCCGCGGAAATGATCAGAAGACGTGCGAATTCCTCAGGGATTAT
TGTGGCCACGAAGGACAACGTTAAAACC
GTTGATTCTTTCATGATGAATTTTGGGAAAAGCACACGCTGTCAGTTCAAGAG
GTTATTCATTGATGAAGGGTTGATGTT
GCATACTGGTTGTGTTAATTTTCTTGTGGCGATGTCATTGTGCGAAATTGCAT
ATGTTTACGGAGACACACAGCAGATTC
CATACATCAATAGAGTTTCAGGATTCCCGTACCCCGCCCATTTTGCCAAATTG
GAAGTTGACGAGGTGGAGACACGCAGA
ACTACTCTCCGTTGTCCAGCCGATGTCACACATTATCTGAACAGGAGATATGA
GGGCTTTGTCATGAGCACTTCTTCGGT
TAAAAAGTCTGTTTCGCAGGAGATGGTCGGCGGAGCCGCCGTGATCAATCCG
ATCTCAAAACCCTTGCATGGCAAGATCC
TGACTTTTACCCAATCGGATAAAGAAGCTCTGCTTTCAAGAGGGTATTCAGAT
GTTCACACTGTGCATGAAGTGCAAGGC
GAGACATACTCTGATGTTTCACTAGTTAGGTTAACCCCTACACCGGTCTCCAT
CATTGCAGGAGACAGCCCACATGTTTT
GGTCGCATTGTCAAGGCACACCTGTTCGCTCAAGTACTACACTGTTGTTATGG
ATCCTTTAGTTAGTATCATTAGAGATC
TAGAGAAACTTAGCTCGTACTTGTTAGATATGTATAAGGTCGATGCAGGAAC
ACAATAGCAATTACAGATTGACTCGGTG
TTCAAAGGTTCCAATCTTTTTGTTGCAGCGCCAAAGACTGGTGATATTTCTGA
TATGCAGTTTTACTATGATAAGTGTCT
CCCAGGCAACAGCACCATGATGAATAATTTTGATGCTGTTACCATGAGGTTG
ACTGACATTTCATTGAATGTCAAAGATT
```

Figure 6b

GCATATTGGATATGTCTAAGTCTGTTGCTGCACCTAAGGATCAAATCAAACCA
CTAATACCTATGGTACGAACGGCGGCA
GAAATGCCACGCCAGACTGGACTATTGGAAAATTTAGTGGCGATGATTAAAA
GAAACTTTAACGCACCCGAGTTGTCTGG
CATCATTGATATTGAAAATACTGCATCTTTGGTTGTAGATAAGTTTTTTGATA
GTTATTTGCTTAAAGAAAAAAGAAAAC
CAAATAAAAATGTTTCTTTGTTCAGTAGAGAGTCTCTCAATAGATGGTTAGAA
AAGCAGGAACAGGTAACAATAGGCCAG
CTCGCAGATTTTGATTTGTGGATTTGCCAGCAGTTGATCAGTACAGACACAT
GATTAAAGCACAACCCAAACAAAAGTT
GGACACTTCAATCCAAACGGAGTACCCGGCTTTGCAGACGATTGTGTACCAT
TCAAAAAAGATCAATGCAATATTCGGCC
CGTTGTTTAGTGAGCTTACTAGGCAATTACTGGACAGTGTTGATTCGAGCAGA
TTTTTGTTTTTCACAAGAAAGACACCA
GCGCAGATTGAGGATTTCTTCGGAGATCTCGACAGTCATGTGCCGATGGATG
TCTTGGAGCTGGATATATCAAAATACGA
CAAATCTCAGAATGAATTCCACTGTGCAGTAGAATACGAGATCTGGCGAAGA
TTGGGTTTCGAAGACTTCTTGGGAGAAG
TTTGGAAACAAGGGCATAGAAAGACCACCCTCAAGGATTATACCGCAGGTAT
AAAAACTTGCATCTGGTATCAAAGAAAG
AGCGGGGACGTCACGACGTTCATTGGAAACACTGTGATCATTGCTGCATGTTT
GGCCTCGATGCTTCCGATGGAGAAAAT
AATCAAAGGAGCCTTTTGCGGTGACGATAGTCTGCTGTACTTTCCAAAGGGTT
GTGAGTTCCGGATGTGCAACACTCCG
CGAATCTTATGTGGAATTTTGAAGCAAAACTGTTTAAAAAACAGTATGGATA
CTTTTGCGGAAGATATGTAATACATCAC
GACAGAGGATGCATTGTGTATTACGATCCCCTAAAGTTGATCTCGAAACTTG
GTGCTAAACACATCAAGGATTGGGAACA
CTTGGAGGAGTTCAGAAGGTCTCTTTGTGATGTTGCTGTTTCGTTGAACAATT
GTGCGTATTACACACAGTTGGACGACG
CTGTATGGGAGGTTCATAAGACCGCCCCTCCAGGTTCGTTTGTTTATAAAAGT
CTGGTGAAGTATTTGTCTGATAAAGTT
CTTTTTAGAAGTTTGTTTATAGATGGCTCTAGTTGTTAAAGGAAAAGTGAATA
TCAATGAGTTTATCGACCTGACAAAAA
TGGAGAAGATCTTACCGTCGATGTTTACCCCTGTAAAGAGTGTTATGTGTTCC
AAAGTTGATAAAATAATGGTTCATGAG
AATGAGTCATTGTCAGGGGTGAACCTTCTTAAAGGAGTTAAGCTTATTGATAG
TGGATACGTCTGTTTAGCCGGTTTGGT
CGTCACGGGCGAGTGGAACTTGCCTGACAATTGCAGAGGAGGTGTGAGCGTG
TGTCTGGTGGACAAAAGGATGGAAAGAG
CCGACGAGGCCATTCTCGGATCTTACTACACAGCAGCTGCAAAGAAAAGATT
TCAGTTCAAGGTCGTTCCCAATTATGCT
ATAACCACCCAGGACGCGATGAGAAACGTCTGGCAAGTTTTAGTTAATATTA
GAAATGTGAAGATGTCAGCGGGTTTCTG
TCCGCTTTCTCTGGAGTTTGTGTCGGTGTGTATTGTTTATAGAAATAATATAA
AATTAGGTTTGAGAGAGAAGATTACAA

Figure 6c

ACGTGAGAGACGGAGGGCCCATGGAACTTACAGAAGAAGTCGTTGATGAGTT
CATGGAAGATGTCCCTATGTCGATCAGG
CTTGCAAAGTTTCGATCTCGAACCGGAAAAAGAGTGATGTCCGCAAAGGGA
AAAATAGTAGTAGTGATCGGTCAGTGCC
GAACAAGAACTATAGAAATGTTAAGGATTTTGGAGGAATGAGTTTTAAAAAG
AATAATTTAATCGATGATGATTCGGAGG
CTACTGTCGCCGAATCGGATTCGTTTTAAATAGATCTTACAGTATCACTACTC
CATCTCAGTTCGTGTTCTTGTCAttaa
ttaaATGGCTAGCAAAGGAGAAGAACTTTTCACTGGAGTTGTCCCAATTCTTGTT
GAATTAGATGGTGATGTTAATGGGC
ACAAATTTTCTGTCAGTGGAGAGGGTGAAGGTGATGCTACATACGGAAAGCT
TACACTTAAATTTATTTGCACTACTGGA
AAACTACCTGTTCCATGGCCAACACTTGTCACTACTTTCTCTTATGGTGTTCA
ATGCTTTTCCCGTTATCCGGATCATAT
GAAACGGCATGACTTTTTCAAGAGTGCCATGCCCGAAGGTTATGTACAGGAA
CGCACTATATCTTTCAAAGATGACGGGA
ACTACAAGACGCGTGCTGAAGTCAAGTTTGAAGGTGATACCCTTGTTAATCG
TATCGAGTTAAAAGGTATTGATTTTAAA
GAAGATGGAAACATTCTCGGACACAAACTCGAGTACAACTATAACTCACACA
ATGTATACATCACGGCAGACAAACAAAA
GAATGGAATCAAAGCTAACTTCAAAATTCGCCACAACATTGAAGATGGATCC
GTTCAACTAGCAGACCATTATCAACAAA
ATACTCCAATTGGCGATGGCCCTGTCCTTTTACCAGACAACCATTACCTGTCG
ACACAATCTGCCCTTTCGAAAGATCCC
AACGAAAAGCGTGACCACATGGTCCTTCTTGAGTTTGTAACTGCTGCTGGGAT
TACACATGGCATGGATGAGCTCTACAA
ATAATGACACTCGAGGGGTAGTCAAGATGCATAATAAATAACGGATTGTGTC
CGTAATCACACGTGGTGCGTACGATAAC
GCATAGTGTTTTCCCTCCACTTAAATCGAAGGGTTGTGTCTTGGATCGCGCG
GGTCAAATGTATATGGTTCATATACAT
CCGCAGGCACGTAATAAAGCGAGGGGTTCGGGTCGAGGTCGGCTGTGAAACT
CGAAAAGGTTCCGGAAAACAAAAAGAG
AGTGGTAGGTAATAGTGTTAATAATAAGAAAATAAATAATAGTGGTAAGAAA
GGTTTGAAAGTTGAGGAAATTGAGGATA
ATGTAAGTGATGACGAGTCTATCGCGTCATCGAGTACGTTTTAATCAATATGC
CTTATACAATCAACTCTCCGAGCCAAT
TTGTTTACTTAAGTTCCGCTTATGCAGATCCTGTGCAGCTGATCAATCTGTGT
ACAAATGCATTGGGTAACCAGTTTCAA
ACGCAACAAGCTAGGACAACAGTCCAACAGCAATTTGCGGATGCCTGGAAAC
CTGTGCCTAGTATGACAGTGAGATTTCC
TGCATCGGATTTCTATGTGTATAGATATAATTCGACGCTTGATCCGTTGATCA
CGGCGTTATTAAATAGCTTCGATACTA
GAAATAGAATAATAGAGGTTGATAATCAACCCGCACCGAATACTACTGAAAT
CGTTAACGCGACTCAGAGGGTAGACGAT
GCGACTGTAGCTATAAGGGCTTCAATCAATAATTTGGCTAATGAACtGGTTCG
TGGAACTGGCaTGTTCAATCAAGCAAG

Figure 6d

CTTTGAGACTGCTAGTGGACTTGTCTGGACCACAACTCCGGCTACTTAGctattgtt
gtgagatttcctaaaataaagtc
actgaagacttaaaattcagggtggctgataccaaaatcagcagtggttgttcgtccacttaaatataacgattgtcata
tctggatccaacagttaaaccatgtgatggtgtatactgtggtatggcgtaaaacaacggaaaagtcgctgaagacttaa
aattcagggtggctgataccaaaatcagcagtggttgttcgtccacttaaaaataacgattgtcatatctggatccaaca
gttaaaccatgtgatggtgtatactgtggtatggcgtaaaacaacggagaggttcgaatcctcccctaaccgcgggtagc
ggccca

Schematic map of location of mutations in BSG 1057.
30K = movement protein; GFP = green fluorescent protein;
CP = coat protein. Nucleotide positions of BSG 1057 mutations
are noted.

VIRAL EXPRESSION VECTORS

CROSS-REFERENCE TO RELATED APPLICATION

This application claims the priority benefit of provisional U.S. Patent Application Serial No. 60/132,697, filed May 4, 1999, pending, which is hereby incorporated herein by reference in its entirety.

TECHNICAL FIELD

This invention is in the field of plant virology. Specifically, the invention relates to the synthesis of nucleic acid sequences encoding an altered viral movement protein, construction of viral vectors expressing such protein, and generation of host plants infected by the viral vectors. The viral vectors permit rapid local and systemic invasion of a host, and allow stable expression of a transgene of interest.

BACKGROUND OF THE INVENTION

In the last fifteen years, considerable progress has been made in expressing foreign genes in plants. Foreign proteins are now routinely produced in many plant species for modification of the plant or for production of proteins for use after extraction. Vectors for the genetic manipulation of plants have been derived from several naturally occurring plant viruses. For the production of specific proteins, transient expression of foreign genes in plants using virus-based vectors has several advantages. Products of plant viruses are among the highest produced proteins in plants. Often a viral gene product is the major protein produced in plant cells during virus replication. Many viruses are able to systemically move from an initial infection site to almost all cells of the plant. Because of these reasons, plant viruses have been developed into efficient transient expression vectors for foreign genes in plants. Viruses of multi-cellular plants are relatively small, probably due to the size limitation in the pathways that allow viruses to move to adjacent cells in the systemic infection of entire plants. One such plant virus upon which plant expression vectors are based is TMV (tobacco mosaic virus). TMV is the type member of the tobamovirus group. TMV has straight tubular virions of approximately 300×18 nm with a 4 nm-diameter hollow canal consisting of approximately 2000 units of a single capsid protein wound helically around a single RNA molecule. Virion particles are 95% protein and 5% RNA by weight. The genome of TMV is composed of a single-stranded RNA of 6395 nucleotides containing five large ORFs. Expression of each gene is regulated independently. The virion RNA serves as the messenger RNA (mRNA) for the 5' genes, encoding the 126 kDa replicase subunit and the overlapping 183 kDa replicase subunit that is produced by read through of an amber stop codon approximately 5% of the time. Expression of the internal genes is controlled by different promoters on the minus-sense RNA that direct synthesis of 3'-coterminal subgenomic mRNAs which are produced during replication. A detailed description of tobamovirus gene expression and life cycle can be found, among other places, in Dawson and Lehto, *Advances in Virus Research* 38:307–342(1991).

Thus, it is of scientific and commercial interest to provide new and improved vectors for the genetic manipulation of plants.

SUMMARY OF THE INVENTION

A principal aspect of the present invention is the design of a recombinant viral vector expressing an altered movement protein and altered 126/183 viral proteins to affect stable expression of a transgene in a plant host.

Accordingly, the present invention provides an isolated nucleic acid sequence encoding an altered viral movement protein having the amino acid sequence shown in SEQ ID NOS.: 5 and 6 and altered 126/183 viral proteins. In one aspect, the isolated nucleic acid sequence is essentially identical to the sequence shown in SEQ ID NOS.: 3 and 4, and it contains a Thymine (T) or Uracil (U) residue at position 5213 and Guanine (G) residue at 5303 as shown in FIG. 1A. In another aspect, the isolated nucleic acid sequence is identical to the sequence shown in SEQ ID NOS.: 3 and 4. The alteration of the 30K movement protein and alteration of the 126/183 viral proteins results in an enhanced ability to facilitate stabilization of a transgene contained in a viral vector.

In a separate embodiment, the present invention provides a viral vector comprising the nucleic acid sequence encoding an altered viral movement protein having the amino acid sequence shown in SEQ ID NOS.: 5 and 6 and altered 126/183 viral proteins. In one aspect, the viral vector exhibits an enhanced ability compared to a control viral vector to stabilize a transgene contained in the vector. Preferably, the vector is a tobacco mosaic viral vector. A particularly preferred vector is designated BSG1057 (deposited with American Type Culture Collection having accession number 20398, which was deposited on Apr. 28, 1999).

In a separate aspect within this embodiment, the viral vector comprises a transgene of interest. Preferably the transgene is a non-viral gene encoding a protein selected from the group consisting of a membrane protein, a cytosolic protein, a secreted protein, a nuclear protein, and a chaperon protein.

The present invention also provides a cell transformed with a subject viral vector. The transformed cell may be animal or plant. Preferably, the cell is a plant cell. The present invention further provides a transgenic plant comprising the viral vector. Preferred transgenic plant may, for example, be *Nicotiana benthamiana* or *Nicotiana tabacum*, but others may be just as readily substituted by one of skill in the art.

BRIEF DESCRIPTION OF THE DRAWINGS

FIG. 1A depicts a first portion of comparison of the nucleotide sequences encoding an altered movement protein contained in the vector BSG1057 (SEQ ID NO.: 4) and the wildtype movement protein contained in the vector BSG1037 (SEQ ID NO.: 3). Sequence identities are indicated by *, and mismatches are indicated by -.

FIG. 1B depicts a second portion of the comparison depicted in FIG. 1A.

FIG. 2 depicts a comparison of the amino acid sequences encoding an altered movement protein contained in the vector BSG1057 (SEQ ID NO.: 6) and the wildtype movement protein contained in the vector BSG1037 (SEQ ID NO.: 5). Sequence identities are indicated by *, and mismatches are indicated by -.

FIG. 5A shows a first portion of the complete sequence of BSG1037 (SEQ D NO.: 1).

FIG. 5B shows a second portion of the complete sequence of BSG1037 (SEQ ID NO.: 1).

FIG. 5C shows a third portion of the complete sequence of BSG1037 (SEQ ID NO.: 1).

FIG. 5D shows a fourth portion of the complete sequence of BSG1037 (SEQ ID NO.: 1).

FIG. 5E shows a second portion of the complete sequence of BSG1037 (SEQ ID NO.: 1).

FIG. 6A shows a first portion of the complete sequence of BSG1057 (SEQ ID NO.: 2).

FIG. 6B shows a second portion of the complete sequence of BSG1057 (SEQ ID NO.: 2).

FIG. 6C shows a third portion of the complete sequence of BSG1057 (SEQ ID NO.: 2)

FIG. 6D shows a fifth portion of the complete sequence of BSG1057 (SEQ ID NO.: 2).

FIG. 6E shows a fifth portion of the complete sequence of BSG1057 (SEQ ID NO.: 2)

FIG. 7 is a schematic map of locations of mutations in BSG1057.

MODES FOR CARRYING OUT THE INVENTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains. For example, the general teaching for constructing viral plant vectors and using them to systemically infect plants and express heterologous proteins therefrom is disclosed in U.S. Pat. Nos. 5,316,931; 5,977,438; 5,889,191; 5,889,190; 5,866,785 and 5,816,653, the entire disclosures of which are hereby incorporated herein by reference.

General Techniques

The practice of the present invention will employ, unless otherwise indicated, conventional techniques of immunology, biochemistry, chemistry, molecular biology, microbiology, cell biology, genomics and recombinant DNA, which are within the skill of the art. See, e.g., Matthews, PLANT VIROLOGY, $3^{rd}$ edition (1991); Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

Definitions

A "plant cell" refers to the structural and physiological unit of plants, consisting of a protoplast and the cell wall.

A "protoplast" is an isolated cell without cell walls, having the potency for regeneration into cell culture, tissue or whole plant.

A "host" encompasses cell, tissue or organism capable of replicating a vector or viral nucleic acid and which is capable of being infected by a virus containing the viral vector or viral nucleic acid. This term is intended to include prokaryotic and eukaryotic cells, organs, tissues, organisms, or in vitro extracts thereof, where appropriate. A preferred host cell is a plant cell.

The term "infection" refers to the process of transferring or the ability of a virus to transfer its nucleic acid to a host, wherein the viral nucleic acid is replicated, viral proteins are synthesized, or new viral particles assembled.

The "movement protein" of tobacco mosaic virus is a noncapsid protein required for cell-to-cell movement of the RNA replicons or viruses in plants.

The terms "nucleic acid sequence", "polynucleotide", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

A "gene" refers to a polynucleotide containing at least one open reading frame that is capable of encoding a particular protein after being transcribed and translated.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as gene product. If the polynucleotide is derived from genomic DNA, expression may include splicing of the mRNA in an eukaryotic cell.

In the context of polynucleotides, a "linear sequence" or a "sequence" is an order of nucleotides in a polynucleotide in a 5' to 3' direction in which residues that neighbor each other in the sequence are contiguous in the primary structure of the polynucleotide.

A linear sequence of nucleotides is "essentially identical" to another linear sequence, if both sequences are capable of hybridizing to form a duplex with the same complementary polynucleotide. Sequences that hybridize under conditions of greater stringency are more preferred. It is understood that hybridization reactions can accommodate insertions, deletions, and substitutions in the nucleotide sequence. Thus, linear sequences of nucleotides can be essentially identical even if some of the nucleotide residues do not precisely correspond or align. In general, essentially identical sequences of about 40 nucleotides in length will hybridize at about 30° C. in 10×SSC (0.15 M NaCl, 15 mM citrate buffer); preferably, they will hybridize at about 40° C. in 6×SSC; more preferably, they will hybridize at about 50°

Figure 3:
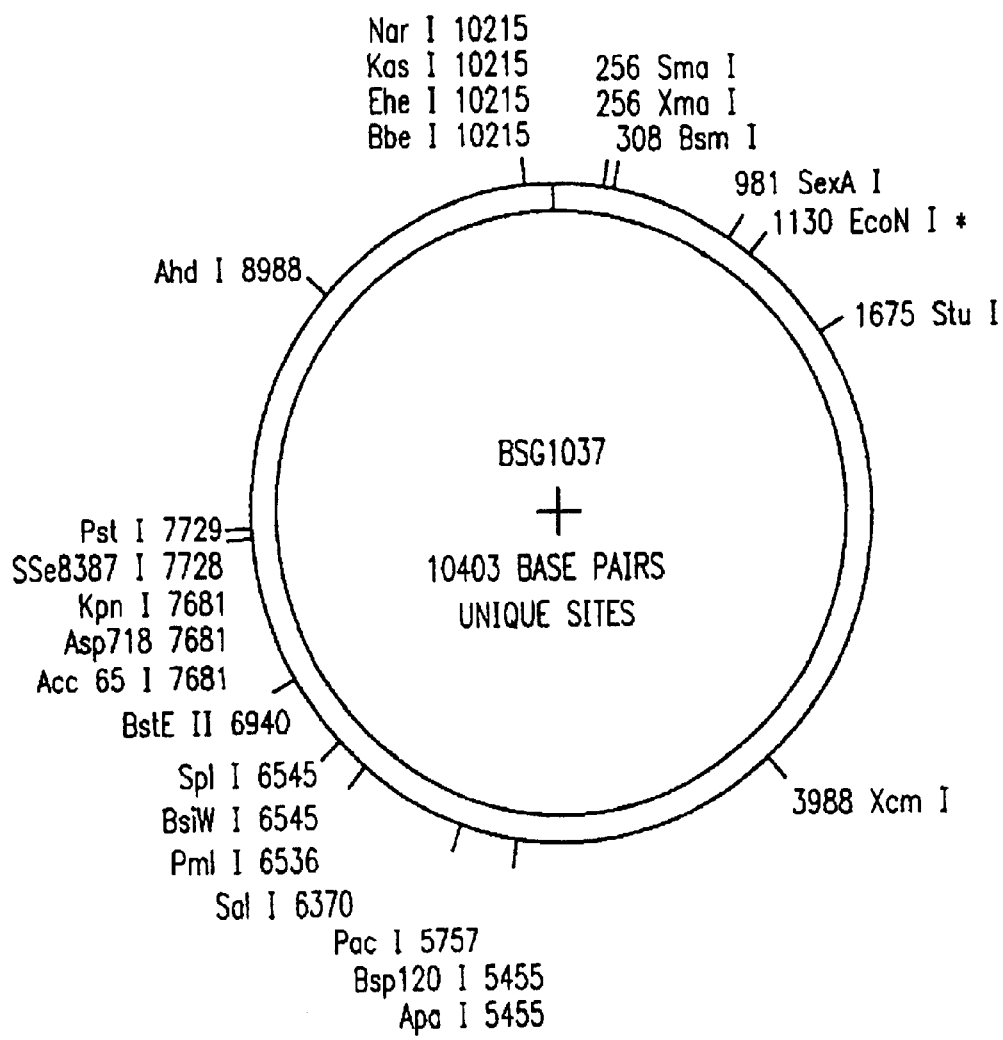
FIG. 3 is a schematic representation of the restriction sites of the vector BSG1037.
Figure 4:
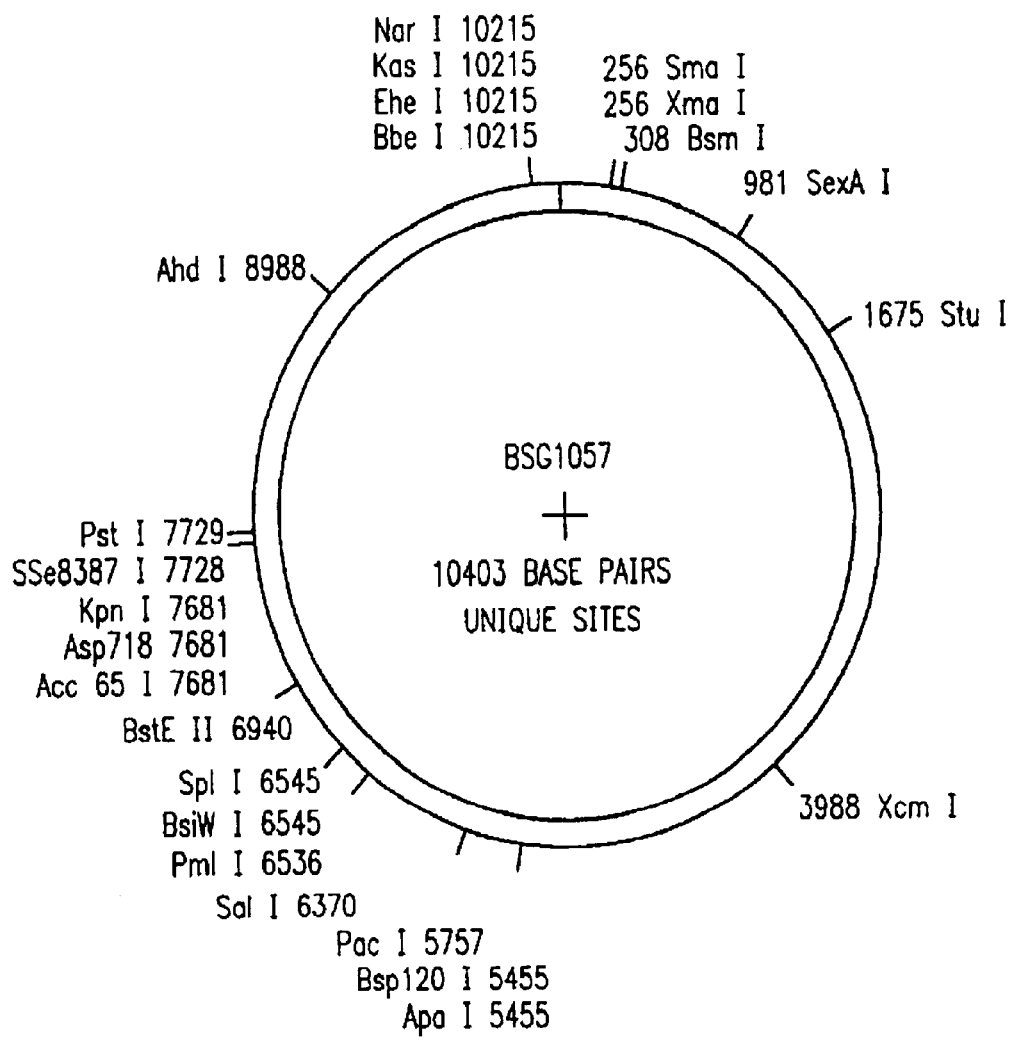
FIG. 4 is a schematic representation of the restriction sites of the vector BSG1057.
Figure 8:
FIG. 8 shows *N. benthamiana* plants at 20 days postinoculation. There are four columns of five plants. The first column on the left shows plants inoculated with first passage BSG1037. Column 2 is seventh passage BSG1037, Column 3 is first passage BSG1057, Column 4 is seventh passage BSG1057.

C. in 6×SSC; even more preferably, they will hybridize at about 60° C. in 6×SSC, or at about 40° C. in 0.5×SSC, or at about 30° C. in 6×SSC containing 50% formamide; still more preferably, they will hybridize at 40° C. or higher in 2×SSC or lower in the presence of 50% or more formamide. It is understood that the rigor of the test is partly a function of the length of the polynucleotide; hence shorter polynucleotides with the same homology should be tested under lower stringency and longer polynucleotides should be tested under higher stringency, adjusting the conditions accordingly. The relationship between hybridization stringency, degree of sequence identity, and polynucleotide length is known in the art and can be calculated by standard formulae; see, e.g., Meinkoth et al. Sequences that correspond or align more closely to the invention disclosed herein are comparably more preferred. Generally, essentially identical sequences are at least about 50% identical with each other, after alignment of the homologous regions. Preferably, the sequences are at least about 60% identical; more preferably, they are at least about 70% identical; more preferably, they are at least about 80% identical; more preferably, the sequences are at least about 90% identical; even more preferably, they are at least 95% identical; still more preferably, the sequences are 100% identical.

In determining whether polynucleotide sequences are essentially identical, a sequence that preserves the functionality of the polynucleotide with which it is being compared is particularly preferred. Functionality may be established by different criteria, such as ability to hybridize with a target polynucleotide, and whether the polynucleotide encodes an identical or essentially identical polypeptides. Thus, nucleotide substitutions which cause a non-conservative substitution in the encoded polypeptide are preferred over nucleotide substitutions that create a stop codon; nucleotide substitutions that cause a conservative substitution in the encoded polypeptide are more preferred, and identical nucleotide sequences are even more preferred. Insertions or deletions in the polynucleotide that result in insertions or deletions in the polypeptide are preferred over those that result in the down-stream coding region being rendered out of phase.

The term "hybridize" as applied to a polynucleotide refers to the ability of the polynucleotide to form a complex that is stabilized via hydrogen bonding between the bases of the nucleotide residues in a hybridization reaction. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these.

The terms "cytosolic", "nuclear" and "secreted" as applied to cellular proteins specify the extracellular and/or subcellular location in which the cellular protein is mostly localized. Certain proteins are "chaperons", capable of translocating back and forth between the cytosol and the nucleus of a cell.

A "control" is an alternative subject or sample used in an experiment for comparison purpose. For example, where the purpose of the experiment is to ascertain whether a viral vector carrying an altered movement protein possesses an enhanced ability in systemic invasion of a host plant, it is generally preferable to use a control viral vector (e.g. BSG1037 shown in FIGS. 1–2) expressing the wildtype altered movement protein (e.g. 1037 sequence shown in FIG. 2).

A "cell line" or "cell culture" denotes bacterial, plant, insect or higher eukaryotic cells grown or maintained in vitro. The descendants of a cell may not be completely identical (either morphologically, genotypically, or phenotypically) to the parent cell.

A "vector" refers to a recombinant plasmid or virus that comprises a polynucleotide to be delivered into a host cell, either in vitro or in vivo. The polynucleotide to be delivered may comprise a coding sequence of interest in gene therapy. nucleic acid molecule, preferably self-replicating, which transfers an inserted nucleic acid molecule into and/or between host cells. The term includes vectors that function primarily for insertion of a DNA or RNA into a cell, replication of vectors that function primarily for the replication of DNA or RNA, and expression vectors that function for transcription and/or translation of the DNA or RNA. Also included are vectors that provide more than one of the above functions.

A "replicon" refers to a polynucleotide comprising an origin of replication (generally referred to as an ori sequence) which allows for replication of the polynucleotide in an appropriate host cell. Examples of replicons include episomes (such as plasmids), as well as chromosomes (such as the nuclear or mitochondrial chromosomes).

A "transcription unit" is a DNA segment capable of directing transcription of a gene or fragment thereof. Typically, a transcription unit comprises a promoter operably linked to a gene or a DNA fragment that is to be transcribed, and optionally regulatory sequences located either upstream or downstream of the initiation site or the termination site of the transcribed gene or fragment.

Nucleic Acids of the Present Invention

The present invention encompasses a recombinant viral vector expressing an altered movement protein and altered 126/183 viral proteins to effect stable expression of a transgene in a plant host. Distinguished from the previously described movement protein, the altered protein contains two amino acid substitutions (replacing the threonine residue at position 104 with isoleucine, and replacing the lysine residue at position 134 with arginine, see FIG. 2). The altered viral vector exhibits an enhanced ability to facilitate stabilization of a transgene contained in a virus that expresses the altered movement protein.

In one embodiment, the present invention provides an isolated nucleic acid sequence encoding an altered viral movement protein having the amino acid sequence shown in SEQ ID NOS.: 5and 6 and altered 126/183 viral proteins. In one aspect within this embodiment, the isolated nucleic acid sequence of the movement protein is essentially identical to the sequence shown in SEQ ID NO. 3, and it contains a Thymine (T) or Uracil (U) residue at position 5213 and Guanine (G) residue at 5303 as shown in FIG. 1A. As used herein, a linear sequence of nucleotides is "essentially identical" to another linear sequence, if both sequences are capable of hybridizing to form a duplex with the same complementary polynucleotide.

Hybridization can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. In general, a low stringency hybridization reaction is carried out at about 40° C. in 6×SSC or a solution of equivalent ionic strength/temperature. A moderate stringency hybridization is typically performed at about 50° C. in 6×SSC, and a high stringency hybridization reaction is generally performed at about 60° C. in 6×SSC. The essentially identical nucleic acid sequences embodiment in the invention encompass all sequences encoding modified movement proteins containing conservative or non-conservative substitutions that do not significantly affect the claimed structural characteristics (i.e. retain the substitution of isoleucine for threonine$_{104}$, and arginine for lysine$_{134}$). Modification of polypeptides by altering their corresponding nucleic acid sequences is routine practice in the art. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. Changes in nucleic acid sequence that do not change the encoded amino acid sequence are generally preferred.

The recombinant viral vector embodiment of this invention comprises a nucleic acid sequence encoding the above-described viral movement protein.

In one embodiment, a nucleic acid is introduced into a plant host. Preferably, the nucleic acid may be introduced by way of a viral nucleic acid, using technques known in the art, and preferably the techniques disclosed in U.S. Pat. Nos. 5,316,931; 5,977,438; 5,889,191; 5,889,190; 5,866,785 and 5,816,653, the entire disclosures of which are hereby incorporated herein by reference. Such recombinant viral nucleic acids are stable for the maintenance and transcription of such nonnative sequences in the plant host.

BSG1057 (SEQ ID NO.:2) is a mutant version of BSG1037 (SEQ ID NO.:1). The complete sequences of BSG1057 and BSG1037 are shown in FIG. 5 and FIG. 6. BSG1037 has improved insert retention properties.

The difference between these two virus vectors is best demonstrated with the Green Fluorescent Protein (GFP) reporter gene. Both BSG1037 and BSG1057 express GFP which can be visualized under long wave UV light by its green fluorescence. The presence of GFP activity identifies those cells in which the recombinant virus is expressing genes.

Nicotiana benthamiana plants inoculated with BSG1037 and BSG1057 were observed under long wave UV light at approximately 4 to 5 days post inoculation. The GFP spots on the leaves of plants inoculated with the BSG1057 virus were noticeably larger than the GFP spots on the leaves of plants inoculted with the BSG1037 virus, indicating the 1057 virus moves cell to cell faster than BSG1037.

Sequence Comparison Between BSG1037 and BSG1057

The specific nucleotide changes between 1037 and 1057 are listed in the table below. In those cases where the nucleotide change resulted in an amino acid change, that change is noted (using the single letter code).

| nt position | 1037 nt | 1057 nt | 1037 AA | 1057 AA |
|---|---|---|---|---|
| 1138 | A | G | E | G |
| 1268 | T | C | No AA changes | |
| 2382 | A | G | K | E |
| 3632 | G | A | No AA changes | |
| 5213 | C | T | T | I |
| 5303 | A | G | K | R |
| 5896 | C | A | No AA changes | |

126/183 refers to the 126/183 viral proteins.
MP refers to the movement protein.

The transgene transcribed by the vector of present invention can be any gene expressed in a biological entity. The selection of transgene is determined largely by the intended purpose of the vector. Preferably the transgene is a non-viral gene selected from the group consisting of a membrane protein, a cytosolic protein, a secreted protein, a nuclear protein, and a chaperon protein.

The vectors embodied in this invention can be obtained using recombinant cloning methods and/or by chemical synthesis. A vast number of recombinant cloning techniques such as PCR, restriction endonuclease digestion and ligation are well known in the art, and need not be described in detail herein. One skilled in the art can also use the sequence data provided herein or that in the public or proprietary databases to obtain a desired vector by any synthetic means available in the art.

Host Cell and Transgenic Organisms of the Present Invention

The invention provides host cells transformed with the viral vectors described above. The host cells may be animal or plant, but plant hosts are preferred. The viral vectors containing a transgene of interest can be introduced into a suitable eukaryotic cell by any of a number of appropriate means, including electroporation, transfection employing calcium chloride, rubidium chloride, calcium phosphate, DEAE-dextran, or other substances; microprojectile bombardment; lipofection; and infection (where the vector is coupled to an infectious agent). The choice of introducing vectors will often depend on features of the host cell.

For plant cells, a variety of techniques derived from these general methods is available in the art. See, for example, U.S. Pat. Nos. 5,316,931; 5,977,438; 5,889,191; 5,889,190; 5,866,785 and 5,816,653. The host cells may be in the form of whole plants, isolated cells or protoplasts. Illustrative procedures for introducing vectors into plant cells include Agrobacterium-mediated plant transformation, protoplast transformation, gene transfer into pollen, injection into reproductive organs and injection into immature embryos, leaf abrasion, abrasion in solution, high velocity water spray, and other injury of a host as well as imbibing host seeds with water containing the recombinant viral RNA or recombinant plant virus. As is evident to one skilled in the art, each of these methods has distinct advantages and disadvantages. Thus, one particular method of introducing genes into a particular plant species may not necessarily be the most effective for another plant species.

Agrobacterium tumefaciens-mediated transfer is a widely applicable system for introducing genes into plant cells because the DNA can be introduced into whole plant tissues, bypassing the need for regeneration of an intact plant from a protoplast. The use of Agrobacterium-mediated expression vectors to introduce DNA into plant cells is well known in the art. This technique makes use of a common feature of Agrobacterium which colonizes plants by transferring a portion of their DNA (the T-DNA) into a host cell, where it becomes integrated into nuclear DNA. The T-DNA is defined by border sequences which are 25 base pairs long, and any DNA between these border sequences is transferred to the plant cells as well. The insertion of a recombinant plant viral nucleic acid between the T-DNA border sequences results in transfer of the recombinant plant viral nucleic acid to the plant cells, where the recombinant plant viral nucleic acid is replicated, and then spreads systemically through the plant. Agro-infection has been accomplished with potato spindle tuber viroid (PSTV) (Gardner et al., *Plant Mol. Biol.* 6:221 (1986); CaV (Grimsley et al., and Lazarowitz, S., *Nucl. Acids Res.* 16:229 (1988)) digitaria streak virus (Donson et al., *Virology* 162:248 (1988)), wheat dwarf virus, and tomato golden mosaic virus (TGMV). Therefore, agro-infection of a susceptible plant could be accomplished with a virion containing a recombinant plant viral nucleic acid based on the nucleotide sequence of any of the above viruses. Particle bombardment or electrosporation or any other methods known in the art may also be used.

Because not all plants are natural hosts for Agrobacterium, alternative methods such as transformation of protoplasts may be employed to introduce the subject vectors into the host cells. For certain monocots, transformation of the plant protoplasts can be achieved using methods based on calcium phosphate precipitation, polyethylene glycol treatment, electroporation, and combinations of these treatments. See, for example, Potrykus et al., *Mol. Gen. Genet.*, 199:169–177 (1985); Fromm et al., *Nature*, 319:791 (1986); and Callis et al., *Genes and Development*, 1:1183 (1987). Applicability of these techniques to different plant species may depend upon the feasibility to regenerate that particular plant species from protoplasts. A variety of methods for the regeneration of cereals from protoplasts are known in the art.

In addition to protoplast transformation, particle bombardment is an alternative and convenient technique for delivering the invention vectors into a plant host cell. Specifically, the plant cells may be bombarded with microparticles coated with a plurality of the subject vectors. Bombardment with DNA-coated microprojectiles has been successfully used to produce stable transformants in both plants and animals (see, for example, Sanford et al. (1993) *Methods in Enzymology*, 217:483–509). Microparticles suitable for introducing vectors into a plant cell are typically made of metal, preferably tungsten or gold. These microparticles are available for example, from BioRad (e.g., Bio-Rad's PDS-1000/He). Those skilled in the art will know that the particle bombardment protocol can be optimized for any plant by varying parameters such as He pressure, quantity of coated particles, distance between the macrocarrier and the stopping screen and flying distance from the stopping screen to the target.

Vectors can also be introduced into plants by direct DNA transfer into pollen as described by Zhou et al., Methods in Enzymology, 101:433 (1983). Other techniques for introducing nucleic acids into a plant cell include:

(a) Hand Inoculations

Hand inoculations are performed using a neutral pH, low molarity phosphate buffer, with the addition of celite or carborundum (usually about 1%). One to four drops of the preparation is put onto the upper surface of a leaf and gently rubbed.

(b) Mechanized Inoculations of Plant Beds

Plant bed inoculations are performed by spraying (gas-propelled) the vector solution into a tractor-driven mower while cutting the leaves. Alternatively, the plant bed is mowed and the vector solution sprayed immediately onto the cut leaves.

(c) High Pressure Spray of Single Leaves

Single plant inoculations can also be performed by spraying the leaves with a narrow, directed spray (50 psi, 6–12 inches from the leaf) containing approximately 1% carborundum in the buffered vector solution.

(d) Vacuum Infiltration

Inoculations may be accomplished by subjecting a host organism to a substantially vacuum pressure environment in order to facilitate infection.

Once introduced into a suitable host cell, expression of the transgene can be determined using any assay known in the art. For example, the presence of transcribed sense or anti-sense strands of the transgene can be detected and/or quantified by conventional hybridization assays (e.g. Northern blot analysis), amplification procedures (e.g. RT-PCR), SAGE (U.S. Pat. No. 5,695,937), and array-based technologies (see e.g. U.S. Pat. Nos. 5,405,783, 5,412,087 and 5,445,934).

Expression of the transgene can also be determined by examining the protein product. A variety of techniques are available in the art for protein analysis. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunoflourescent assays, and PAGE-SDS.

In general, determining the protein level involves (a) providing a biological sample containing polypeptides; and (b) measuring the amount of any immunospecific binding that occurs between an antibody reactive to the trangene product and a component in the sample, in which the amount of immunospecific binding indicates the level of expressed proteins. Antibodies that specifically recognize and bind to the protein products of the transgene are required for immunoassays. These may be purchased from commercial vendors or generated and screened using methods well known in the art. See Harlow and Lane (1988) supra. and Sambrook et al. (1989) supra. The sample of test proteins can be prepared by homogenizing the eukaryotic transformants (e.g. plant cells) or their progenies made therefrom, and optionally solubilizing the test protein using detergents, preferably non-reducing detergents such as triton and digitonin. The binding reaction in which the test proteins are allowed to interact with the detecting antibodies may be performed in solution, or on a solid tissue sample, for example, using tissue sections or solid support that has been immobilized with the test proteins. The formation of the complex can be detected by a number of techniques known in the art. For example, the antibodies may be supplied with a label and unreacted antibodies may be removed from the complex; the amount of remaining label thereby indicating the amount of complex formed. Results obtained using any such assay on a sample from a plant transformant or a progeny thereof is compared with those from a non-transformed source as a control.

The eukaryotic host cells of this invention are grown under favorable conditions to effect transcription of the transgene. The host cells may also be employed to generate transgenic organisms such as transgenic plants comprising the recombinant DNA vectors of the present invention. Preferred host cells are those having the propensity to regenerate into tissue or a whole organisms. Examples of these preferred host cells include certain plant cells exemplified herein.

Accordingly, this invention provides transgenic plants carrying the subject vectors. The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil.

The regeneration of plants containing the subject vector introduced by Agrobacterium tumefaciens from leaf explants can be achieved as described by Fraley et al., *Proc. Natl. Acad. Sci. U.S.A.*, 80:4803 (1983). In this procedure, transformants are grown in the presence of a selection agent and in a medium that induces the regeneration of shoots in the plant species being transformed. This procedure typically produces shoots within two to four weeks and these transformant shoots are then transferred to an appropriate root-inducing medium containing the selective agent and an antibiotic to prevent bacterial growth. Transformant shoots that rooted in the presence of the selective agent to form plantlets are then transplanted to soil to allow the production of roots. These procedures will vary depending upon the particular plant species employed, as is apparent to one of ordinary skill in the art.

A population of progeny can be produced from the first and second transformants of a plant species by methods well known in the art including cross fertilization and asexual reproduction. Transgenic plants embodied in the present invention are useful for production of desired proteins, and as test systems for analysis of the biological functions of a gene.

EXAMPLES

Tobacco plants inoculated with the viruses BSG1037 or BSG1057 express the reporter gene (GFP) in cells that are infected with either virus. The reporter gene activity (indicative of the presence of virus) is easily observed by illuminating plants with long wave UV light. Viruses that lose expression of the inserted gfp gene no longer accumulate the GFP protein and do not exhibit GFP fluorescence under UV illumination.

In order to assess the stability of expression of a foreign gene in the new vector, the gfp gene was introduced into the standard vector (giving rise to BSG1037) and the improved vector (giving rise to BSG1057). RNA transcripts of these constructs was generated and used to inoculate Nicotiana benthamiana plants. At about 7 days postinoculation, extensive systemic GFP expression was observed. GFP-expressing tissue was harvested, ground in phosphate buffer, the cellular debris removed by low-speed centrifugation, and the resulting "green juice" supernatant solution used to inoculate a new set of N. benthamiana plants. Systemic tissue was again harvested at about 7 days and the resulting green juice used to serial passage the virus. The procedure was used to serial passage the viruses a total of 7 times. A comparison was then initiated in which N. benthamiana plants were inoculated in parallel with the first passage green juice and the seventh passage green juice for BSG1037 and BSG1057. The first passage virus gave excellent systemic expression of GFP beginning about 4 days post inoculation. The BSG1037 seventh passage virus gave little systemic GFP expression and strong visual TMV mosaic symptoms characteristic of a vector that has lost most or all of the inserted sequence. In contrast, the BSG1057 seventh passage virus still gave excellent systemic GFP expression and the mild visual viral symptoms characteristic of a vector retaining its inserted gene.

At 20 days post inoculation, the plants were cut 2 inches above the soil line and allowed to regrow. Plants were monitored as to the accumulation of GFP protein in the new systemic tissue up to 3 weeks post cutting. Plants containing the BSG 1037 virus (both first and seventh passage) showed very little GFP in regrowth tissues, while showing extensive virus symptoms. This result indicates that the virus population was dominated by viruses that have recombinationally lost the genetic insertion. Plants containing BSG1057 (both first and seventh passage) showed good systemic invasion in re-growth tissue. This indicates superior genetic stability of the foreign gene insertion, gfp gene, in BSG1057 compared with BSG1037.

This increased genetic stability of foreign genes was also seen using two additional gene insertions: interferon gamma from chickens and human alpha galactosidase A. Serial passage experiments of either gene in BSG1037 virus preparations showed variable production of product in plants, while comparable experiments in BSG1057 showed more uniform product accumulation in plants. These experiments indicate that the BSG1057 retains foreign gene insertions through multiple passages to a greater extent.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. An isolated nucleic acid sequence comprising a nucleic acid sequence encoding an altered viral movement protein having the amino acid sequence shown in SEQ ID NO: 6.

2. The isolated nucleic acid sequence of claim 1 that is identical to the sequence shown in SEQ ID NO: 4.

3. The isolated nucleic acid of claim 1, wherein the altered movement protein enhances the ability to facilitate stabilization of a transgene contained in a virus that expresses the altered movement protein.

4. An isolated nucleic acid sequence comprising a nucleic acid sequence encoding an altered 126/183 replicase complex having a nucleic acid alteration at nucleotide positions 1138, 1268, 2382, and 3632 as shown in SEQ ID NO: 2 .

5. An isolated nucleic acid according to claim 4 wherein the altered 126/183 replicase complex enhances the stabilization of a transgene contained in a virus that expresses the altered replicase complex.

6. A viral vector comprising a nucleic acid sequence encoding an altered viral movement protein having the amino acid sequence shown in SEQ ID NO.: 6.

7. The viral vector of claim 6, further comprising a transgene, wherein said viral vector exhibits an enhanced ability to stabilize said transgene compared to a control viral vector comprising a wild type movement protein as shown in SEQ ID NO: 3.

8. The viral vector of claim 7, wherein the transgene is a non-viral gene.

9. The viral vector of claim 8, wherein the non-viral transgene encodes a protein selected from the group consisting of a membrane protein, a cytosolic protein, a secreted protein, a nuclear protein, and a chaperon protein.

10. The viral vector of claim 6, wherein the vector is a tobacco mosaic viral vector.

11. The viral vector of claim 6 that is designated BSG1057 deposited with American Type Culture Collection accession number 20398.

12. A plant cell transformed with the viral vector of claim 6.

13. An isolated nucleic acid sequence of SEQ ID NO: 1.

14. An isolated nucleic acid sequence of SEQ ID NO: 2.

* * * * *

SEQUENCE LISTING

<160> NUMBER OF SEQ ID NOS: 6

<210> SEQ ID NO 1
<211> LENGTH: 7685
<212> TYPE: DNA
<213> ORGANISM: Nicotiana tabacum

<400> SEQUENCE: 1

```
gtatttttac aacaattacc aacaacaaca aacaacagac aacattacaa ttactattta     60
caattacaat ggcatacaca cagacagcta ccacatcagc tttgctggac actgtccgag    120
gaaacaactc cttggtcaat gatctagcaa agcgtcgtct ttacgacaca gcggttgaag    180
agtttaacgc tcgtgaccgc aggcccaagg tgaacttttc aaaagtaata agcgaggagc    240
agacgcttat tgctacccgg gcgtatccag aattccaaat tacattttat aacacgcaaa    300
atgccgtgca ttcgcttgca ggtggattgc gatctttaga actggaatat ctgatgatgc    360
aaattcccta cggatcattg acttatgaca taggcgggaa ttttgcatcg catctgttca    420
```

-continued

```
agggacgagc atatgtacac tgctgcatgc ccaacctgga cgttcgagac atcatgcggc      480
acgaaggcca gaaagacagt attgaactat acctttctag gctagagaga gggggggaaaa     540 cagtccccaa cttccaaaag gaagcatttg acagatacgc agaaattcct gaagacgctg      600
tctgtcacaa actttccag acatgcgaac atcagccgat gcagcaatca ggcagagtgt       660
atgccattgc gctacacagc atatatgaca taccagccga tgagttcggg gcggcactct      720
tgaggaaaaa tgtccatacg tgctatgccg cttttccactt ctccgagaac ctgcttcttg     780
aagattcatg cgtcaatttg gacgaaatca acgcgtgttt ttcgcgcgat ggagacaagt      840 tgacctttc ttttgcatca gagagtactc ttaattactg tcatagttat tctaatattc       900
ttaagtatgt gtgcaaaact tacttcccgg cctctaatag agaggtttac atgaaggagt      960
ttttagtcac cagagttaat acctggtttt gtaagttttc tagaatagat acttttctt      1020 tgtacaaagg tgtggcccat aaaagtgtag atagtgagca gttttatact gcaatggaag     1080
acgcatggca ttacaaaag actcttgcaa tgtgcaacag cgagagaatc ctccttgagg      1140
attcatcatc agtcaattac tggttttccca aaatgaggga tatggtcatc gtaccattat    1200
tcgacatttc tttggagact agtaagagga cgcgcaagga agtcttagtg tccaaggatt     1260
tcgtgtttac agtgcttaac cacattcgaa cataccaggc gaaagctctt acatacgcaa     1320
atgttttgtc cttcgtcgaa tcgattcgat cgagggtaat cattaacggt gtgacagcga    1380
ggtccgaatg ggatgtggac aaatctttgt tacaatcctt gtccatgacg ttttacctgc     1440
atactaagct tgccgttcta aaggatgact tactgattag caagtttagt ctcggttcga     1500
aaacggtgtg ccagcatgtg tgggatgaga tttcgctggc gtttgggaac gcatttccct     1560
ccgtgaaaga gaggctcttg aacaggaaac ttatcagagt ggcaggcgac gcattagaga    1620
tcagggtgcc tgatctatat gtgaccttcc acgacagatt agtgactgag tacaaggcct    1680
ctgtggacat gcctgcgctt gacattagga agaagatgga agaaacggaa gtgatgtaca    1740
atgcactttc agaattatcg gtgttaaggg agtctgacaa attcgatgtt gatgtttttt    1800
cccagatgtg ccaatctttg gaagttgacc caatgacggc agcgaaggtt atagtcgcgg    1860
tcatgagcaa tgagagcggt ctgactctca catttgaacg acctactgag gcgaatgttg    1920
cgctagcttt acaggatcaa gagaaggctt cagaaggtgc attggtagtt acctcaagag    1980
aagttgaaga accgtccatg aagggttcga tggccagagg agagttacaa ttagctggtc    2040
ttgctggaga tcatccggaa tcgtcctatt ctaagaacga ggagatagag tctttagagc    2100
agtttcatat ggcgacggca gattcgttaa ttcgtaagca gatgagctcg attgtgtaca    2160
cgggtccgat taaagttcag caaatgaaaa actttatcga tagcctggta gcatcactat    2220 ctgctgcgt gtcgaatctc gtcaagatcc tcaaagatac agctgctatt gaccttgaaa     2280
cccgtcaaaa gtttggagtc ttggatgttg catctaggaa gtggttaatc aaaccaacgg    2340
ccaagagtca tgcatggggt gttgttgaaa cccacgcgag gaagtatcat gtggcgcttt    2400
tggaatatga tgagcagggt gtggtgacat gcgatgattg gagaagagta gctgttagct    2460
ctgagtctgt tgtttattcc gacatggcga aactcagaac tctgcgcaga ctgcttcgaa    2520
acggagaacc gcatgtcagt agcgcaaagg ttgttcttgt ggacgagtt ccgggctgtg     2580 gaaaaaccaa gaaaattctt ccagggtta atttttgatga agatctaatt ttagtacctg     2640
ggaagcaagc cgcggaaatg atcagaagac gtgcgaattc ctcagggatt attgtggcca    2700
cgaaggacaa cgttaaaacc gttgattctt tcatgatgaa ttttgggaaa agcacacgct    2760
```

```
gtcagttcaa gaggttattc attgatgaag ggttgatgtt gcatactggt tgtgttaatt      2820
ttcttgtggc gatgtcattg tgcgaaattg catatgttta cggagacaca cagcagattc      2880
catacatcaa tagagtttca ggattcccgt accccgccca ttttgccaaa ttggaagttg      2940
acgaggtgga gacacgcaga actactctcc gttgtccagc cgatgtcaca cattatctga      3000
acaggagata tgagggcttt gtcatgagca cttcttcggt taaaaagtct gtttcgcagg      3060
agatggtcgg cggagccgcc gtgatcaatc cgatctcaaa acccttgcat ggcaagatct      3120
tgacttttac ccaatcggat aaagaagctc tgctttcaag agggtattca gatgttcaca      3180
ctgtgcatga agtgcaaggc gagacatact ctgatgtttc actagttagg ttaaccccta      3240
caccggtctc catcattgca ggagacagcc acatgttttt ggtcgcattg tcaaggcaca      3300
cctgttcgct caagtactac actgttgtta tggatccttt agttagtatc attagagatc      3360
tagagaaact tagctcgtac ttgttagata tgtataaggt cgatgcagga acacaatagc      3420
aattacagat tgactcggtg ttcaaaggtt ccaatctttt tgttgcagcg ccaaagactg      3480
gtgatatttc tgtatgcag ttttactatg ataagtgtct cccaggcaac agcaccatga      3540
tgaataattt tgatgctgtt accatgaggt tgactgacat ttcattgaat gtcaaagatt      3600
gcatattgga tatgtctaag tctgttgctg cgcctaagga tcaaatcaaa ccactaatac      3660
ctatggtacg aacggcggca gaaatgccac gccagactgg actattggaa aatttagtgg      3720
cgatgattaa aagaaacttt aacgcacccg agttgtctgg catcattgat attgaaaata      3780
ctgcatcttt ggttgtagat aagttttttg atagttattt gcttaaagaa aaagaaaac      3840 caaataaaaa tgtttctttg ttcagtagag agtctctcaa tagatggtta gaaaagcagg      3900
aacaggtaac aataggccag ctcgcagatt ttgattttgt ggatttgcca gcagttgatc      3960
agtacagaca catgattaaa gcacaaccca acaaaagtt ggacacttca atccaaacgg      4020
agtacccggc tttgcagacg attgtgtacc attcaaaaaa gatcaatgca atattcggcc      4080
cgttgtttag tgagcttact aggcaattac tggacagtgt tgattcgagc agattttgt      4140 ttttcacaag aaagacacca gcgcagattg aggatttctt cggagatctc gacagtcatg      4200
tgccgatgga tgtcttggag ctggatatat caaaatacga caaatctcag aatgaattcc      4260
actgtgcagt agaatacgag atctggcgaa gattgggttt cgaagacttc ttgggagaag      4320
tttggaaaca agggcataga aagaccaccc tcaaggatta taccgcaggt ataaaaactt      4380
gcatctggta tcaaagaaag agcggggacg tcacgacgtt cattggaaac actgtgatca      4440
ttgctgcatg tttggcctcg atgcttccga tggagaaaat aatcaaagga gccttttgcg      4500
gtgacgatag tctgctgtac tttccaaagg gttgtgagtt tccggatgtg caacactccg      4560
cgaatcttat gtggaatttt gaagcaaaac tgtttaaaaa acagtatgga tacttttgcg      4620
gaagatatgt aatacatcac gacagaggat gcattgtgta ttacgatccc ctaaagttga      4680
tctcgaaact tggtgctaaa cacatcaagg attgggaaca cttggaggag ttcagaaggt      4740
ctctttgtga tgttgctgtt tcgttgaaca attgtgcgta ttacacacag ttggacgacg      4800
ctgtatggga ggttcataag accgcccctc caggttcgtt tgtttataaa agtctggtga      4860
agtatttgtc tgataaagtt cttttttagaa gtttgtttat agatggctct agttgttaaa      4920
ggaaaagtga atatcaatga gtttatcgac ctgacaaaaa tggagaagat cttaccgtcg      4980
atgtttaccc ctgtaaagag tgttatgtgt tccaaagttg ataaaataat ggttcatgag      5040
aatgagtcat tgtcagggt gaaccttctt aaaggagtta agcttattga tagtggatac      5100
gtctgtttag ccggtttggt cgtcacgggc gagtggaact tgcctgacaa ttgcagagga      5160
```

```
ggtgtgagcg tgtgtctggt ggacaaaagg atggaaagag ccgacgaggc cactctcgga   5220
tcttactaca cagcagctgc aaagaaaaga tttcagttca aggtcgttcc caattatgct   5280
ataaccaccc aggacgcgat gaaaaacgtc tggcaagttt tagttaatat tagaaatgtg   5340
aagatgtcag cgggtttctg tccgctttct ctggagtttg tgtcggtgtg tattgtttat   5400
agaaataata taaaattagg tttgagagag aagattacaa acgtgagaga cggagggccc   5460
atggaactta cagaagaagt cgttgatgag ttcatggaag atgtccctat gtcgatcagg   5520
cttgcaaagt ttcgatctcg aaccggaaaa agagtgatg tccgcaaagg gaaaatagt   5580 agtagtgatc ggtcagtgcc gaacaagaac tatagaaatg ttaaggattt tggaggaatg   5640
agttttaaaa agaataattt aatcgatgat gattcggagg ctactgtcgc cgaatcggat   5700 tcgtttaaa tagatcttac agtatcacta ctccatctca gttcgtgttc ttgtcattaa   5760
ttaaatggct agcaaaggag aagaactttt cactggagtt gtcccaattc ttgttgaatt   5820
agatggtgat gttaatgggc acaaattttc tgtcagtgga gagggtgaag gtgatgctac   5880
atacggaaag cttacccctta aatttatttg cactactgga aaactacctg ttccatggcc   5940
aacacttgtc actactttct cttatggtgt tcaatgcttt tcccgttatc cggatcatat   6000
gaaacggcat gactttttca agagtgccat gcccgaaggt tatgtacagg aacgcactat   6060
atctttcaaa gatgacggga actacaagac gcgtgctgaa gtcaagtttg aaggtgatac   6120
ccttgttaat cgtatcgagt taaaggtat tgattttaaa gaagatggaa acattctcgg   6180
acacaaactc gagtacaact ataactcaca caatgtatac atcacggcag acaaacaaaa   6240
gaatggaatc aaagctaact tcaaaattcg ccacaacatt gaagatggat ccgttcaact   6300
agcagaccat tatcaacaaa atactccaat tggcgatggc cctgtccttt taccagacaa   6360
ccattacctg tcgacacaat ctgccctttc gaaagatccc aacgaaaagc gtgaccacat   6420
gggccttctt gagtttgtaa ctgctgctgg gattacacat ggcatggatg agctctacaa   6480
ataatgacac tcgagggta gtcaagatgc ataataaata acggattgtg tccgtaatca   6540
cacgtggtgc gtacgataac gcatagtgtt tttccctcca cttaaatcga agggttgtgt   6600
cttggatcgc gcgggtcaaa tgtatatggt tcatatacat ccgcaggcac gtaataaagc   6660 gagggggttcg ggtcgaggtc ggctgtgaaa ctcgaaaagg ttccggaaaa caaaaagag   6720 agtggtaggt aatagtgtta ataataagaa aataaataat agtggtaaga aaggtttgaa   6780
agttgaggaa attgaggata atgtaagtga tgacgagtct atcgcgtcat cgagtacgtt   6840
ttaatcaata tgccttatac aatcaactct ccgagccaat ttgttttactt aagttccgct   6900 tatgcagatc ctgtgcagct gatcaatctg tgtacaaatg cattgggtaa ccagtttcaa   6960
acgcaacaag ctaggacaac agtccaacag caatttgcgg atgcctggaa acctgtgcct   7020
agtatgacag tgagatttcc tgcatcggat ttctatgtgt atagatataa ttcgacgctt   7080
gatccgttga tcacggcgtt attaaatagc ttcgatacta gaaatagaat aatagaggtt   7140
gataatcaac ccgcaccgaa tactactgaa atcgttaacg cgactcagag ggtagacgat   7200
gcgactgtag ctataagggc ttcaatcaat aatttggcta atgaactggt tcgtggaact   7260
ggcatgttca atcaagcaag ctttgagact gctagtggac ttgtctggac acaactccg   7320 gctacttagc tattgttgtg agatttccta aaataaagtc actgaagact taaaattcag   7380
ggtggctgat accaaaatca gcagtggttg ttcgtccact taaatataac gattgtcata   7440
tctggatcca acagttaaac catgtgatgg tgtatactgt ggtatggcgt aaaacaacgg   7500
```

-continued

| | |
|---|---|
| aaaagtcgct gaagacttaa aattcaggdt ggctgatacc aaaatcagca gtggttgttc | 7560 |
| gtccacttaa aaataacgat tgtcatatct ggatccaaca gttaaaccat gtgatggtgt | 7620 |
| atactgtggt atggcgtaaa caacggagag gttcgaatcc tcccctaacc gcgggtagcg | 7680 |
| gccca | 7685 |

<210> SEQ ID NO 2
<211> LENGTH: 7686
<212> TYPE: DNA
<213> ORGANISM: Nicotiana tabacum

<400> SEQUENCE: 2

| | |
|---|---|
| gtatttttac aacaattacc aacaacaaca aacaacagac aacattacaa ttactattta | 60 |
| caattacaat ggcatacaca cagacagcta ccacatcagc tttgctggac actgtccgag | 120 |
| gaaacaactc cttggtcaat gatctagcaa agcgtcgtct ttacgacaca gcggttgaag | 180 |
| agtttaacgc tcgtgaccgc aggcccaagg tgaacttttc aaaagtaata agcgaggagc | 240 |
| agacgcttat tgctacccgg gcgtatccag aattccaaat tacattttat aacacgcaaa | 300 |
| atgccgtgca ttcgcttgca ggtggattgc gatctttaga actggaatat ctgatgatgc | 360 |
| aaattcccta cggatcattg acttatgaca taggcgggaa ttttgcatcg catctgttca | 420 |
| agggacgagc atatgtacac tgctgcatgc ccaacctgga cgttcgagac atcatgcggc | 480 |
| acgaaggcca gaaagacagt attgaactat acctttctag gctagagaga ggggggaaaa | 540 |
| cagtccccaa cttccaaaag gaagcatttg acagatacga agaaattcct gaagacgctg | 600 |
| tctgtcacaa tactttccag acatgcgaac atcagccgat gcagcaatca ggcagagtgt | 660 |
| atgccattgc gctacacagc atatatgaca taccagccga tgagttcggg gcggcactct | 720 |
| tgaggaaaaa tgtccatacg tgctatgccg cttccactt ctccgagaac ctgcttcttg | 780 |
| aagattcatg cgtcaatttg gacgaaatca acgcgtgttt ttcgcgcgat ggagacaagt | 840 |
| tgaccttttc ttttgcatca gagagtactc ttaattactg tcatagttat tctaatattc | 900 |
| ttaagtatgt gtgcaaaact tacttcccgg cctctaatag agaggtttac atgaaggagt | 960 |
| ttttagtcac cagagttaat acctggtttt gtaagttttc tagaatagat acttttcttt | 1020 |
| tgtacaaagg tgtggcccat aaaagtgtag atagtgagca gttttatact gcaatggaag | 1080 |
| acgcatggca ttacaaaaag actcttgcaa tgtgcaacag cgagagaatc ctccttgggg | 1140 |
| attcatcatc agtcaattac tggtttccca aaatgaggga tatggtcatc gtaccattat | 1200 |
| tcgacatttc tttggagact agtaagagga cgcgcaagga agtcttagtg tccaaggatt | 1260 |
| tcgtgttcac agtgcttaac cacattcgaa cataccaggc gaaagctctt acatacgcaa | 1320 |
| atgttttgtc cttcgtcgaa tcgattcgat cgagggtaat cattaacggt gtgacagcga | 1380 |
| ggtccgaatg ggatgtggac aaatctttgt tacaatcctt gtccatgacg ttttacctgc | 1440 |
| atactaagct tgccgttcta aaggatgact tactgattag caagtttagt ctcggttcga | 1500 |
| aaacggtgtg ccagcatgtg tgggatgaga tttcgctggc gtttgggaac gcatttccct | 1560 |
| ccgtgaaaga gaggctcttg aacaggaaac ttatcagagt ggcaggcgac gcattagaga | 1620 |
| tcagggtgcc tgatctatat gtgaccttcc acgacagatt agtgactgag tacaaggcct | 1680 |
| ctgtggacat gcctgcgctt gacattagga agaagatgga agaaacggaa gtgatgtaca | 1740 |
| atgcactttc agaattatcg gtgttaaggg agtctgacaa attcgatgtt gatgttttt | 1800 |
| cccagatgtg ccaatctttg gaagttgacc caatgacggc agcgaaggtt atagtcgcgg | 1860 |
| tcatgagcaa tgagagcggt ctgactctca catttgaacg acctactgag gcgaatgttg | 1920 |

-continued

```
cgctagcttt acaggatcaa gagaaggctt cagaaggtgc attggtagtt acctcaagag    1980
aagttgaaga accgtccatg aagggttcga tggccagagg agagttacaa ttagctggtc    2040
ttgctggaga tcatccggaa tcgtcctatt ctaagaacga ggagatagag tctttagagc    2100
agtttcatat ggcgacggca gattcgttaa ttcgtaagca gatgagctcg attgtgtaca    2160
cgggtccgat taaagttcag caaatgaaaa actttatcga tagcctggta gcatcactat    2220
ctgctgcggt gtcgaatctc gtcaagatcc tcaaagatac agctgctatt gaccttgaaa    2280
cccgtcaaaa gtttggagtc ttggatgttg catctaggaa gtggttaatc aaaccaacgg    2340
ccaagagtca tgcatgggt gttgttgaaa cccacgcgag ggagtatcat gtggcgcttt     2400
tggaatatga tgagcaggt gtggtgacat gcgatgattg gagaagagta gctgttagct     2460
ctgagtctgt tgtttattcc gacatggcga aactcagaac tctgcgcaga ctgcttcgaa    2520
acggagaacc gcatgtcagt agcgcaaagg ttgttcttgt ggacggagtt ccgggctgtg    2580
gaaaaaccaa agaaattctt tccagggtta attttgatga agatctaatt ttagtacctg    2640
ggaagcaagc cgcggaaatg atcagaagac gtgcgaattc ctcagggatt attgtggcca    2700
cgaaggacaa cgttaaaacc gttgattctt tcatgatgaa ttttgggaaa agcacacgct    2760
gtcagttcaa gaggttattc attgatgaag ggttgatgtt gcatactggt tgtgttaatt    2820
ttcttgtggc gatgtcattg tgcgaaattg catatgttta cggagacaca cagcagattc    2880
catacatcaa tagagtttca ggattcccgt accccgccca ttttgccaaa ttggaagttg    2940
acgaggtgga gacacgcaga actactctcc gttgtccagc cgatgtcaca cattatctga    3000
acaggagata tgagggcttt gtcatgagca cttcttcggt taaaaagtct gtttcgcagg    3060
agatggtcgg cggagccgcc gtgatcaatc cgatctcaaa acccttgcat ggcaagatcc    3120 tgactttttac ccaatcggat aaagaagctc tgctttcaag agggtattca gatgttcaca   3180
ctgtgcatga agtgcaaggc gagacatact ctgatgtttc actagttagg ttaaccccta    3240
caccggtctc catcattgca ggagacagcc acatgttttt ggtcgcattg tcaaggcaca    3300
cctgttcgct caagtactac actgttgtta tggatccttt agttagtatc attagagatc    3360
tagagaaact tagctcgtac ttgttagata tgtataaggt cgatgcagga acacaatagc    3420
aattacagat tgactcggtg ttcaaaggtt ccaatctttt tgttgcagcg ccaaagactg    3480
gtgatatttc tgatatgcag ttttactatg ataagtgtct cccaggcaac agcaccatga    3540
tgaataattt tgatgctgtt accatgaggt tgactgacat tcattgaat gtcaaagatt     3600 gcatattgga tatgtctaag tctgttgctg cacctaagga tcaaatcaaa ccactaatac    3660
ctatggtacg aacggcggca gaaatgccac gccagactgg actattggaa aatttagtgg    3720
cgatgattaa agaaacttt aacgcacccg agttgtctgg catcattgat attgaaaata     3780
ctgcatcttt ggttgtagat aagtttttg atagttattt gcttaaagaa aaagaaaac     3840 caaataaaaa tgtttctttg ttcagtagag agtctctcaa tagatggtta gaaaagcagg    3900
aacaggtaac aataggccag ctcgcagatt ttgattttgt ggatttgcca gcagttgatc    3960
agtacagaca catgattaaa gcacaaccca acaaaagtt ggacacttca atccaaacgg     4020
agtacccggc tttgcagacg attgtgtacc attcaaaaaa gatcaatgca atattcggcc    4080
cgttgtttag tgagcttact aggcaattac tggacagtgt tgattcgagc agattttgt     4140 ttttcacaag aaagacacca gcgcagattg aggattcttt cggagatctc gacagtcatg    4200
tgccgatgga tgtcttggag ctggatatat caaaatacga caaatctcag aatgaattcc    4260
```

-continued

```
actgtgcagt agaatacgag atctggcgaa gattgggttt cgaagacttc ttgggagaag      4320
tttggaaaca agggcataga aagaccaccc tcaaggatta taccgcaggt ataaaaactt      4380
gcatctggta tcaaagaaag agcggggacg tcacgacgtt cattggaaac actgtgatca      4440
ttgctgcatg tttggcctcg atgcttccga tggagaaaat aatcaaagga gccttttgcg      4500
gtgacgatag tctgctgtac tttccaaagg gttgtgagtt tccggatgtg caacactccg      4560
cgaatcttat gtggaatttt gaagcaaaac tgtttaaaaa acagtatgga tacttttgcg      4620
gaagatatgt aatacatcac gacagaggat gcattgtgta ttacgatccc ctaaagttga      4680
tctcgaaact tggtgctaaa cacatcaagg attgggaaca cttggaggag ttcagaaggt      4740
ctctttgtga tgttgctgtt tcgttgaaca attgtgcgta ttacacacag ttggacgacg      4800
ctgtatggga ggttcataag accgccctc caggttcgtt tgtttataaa agtctggtga      4860
agtatttgtc tgataaagtt ctttttagaa gtttgtttat agatggctct agttgttaaa      4920
ggaaaagtga atatcaatga gtttatcgac ctgacaaaaa tggagaagat cttaccgtcg      4980
atgtttaccc ctgtaaagag tgttatgtgt tccaaagttg ataaaataat ggttcatgag      5040
aatgagtcat tgtcagggt gaaccttctt aaaggagtta agcttattga tagtggatac      5100
gtctgtttag ccggtttggt cgtcacgggc gagtggaact tgcctgacaa ttgcagagga      5160
ggtgtgagcg tgtgtctggt ggacaaaagg atggaaagag ccgacgaggc cattctcgga      5220
tcttactaca cagcagctgc aaagaaaaga tttcagttca aggtcgttcc caattatgct      5280
ataaccaccc aggacgcgat gagaaacgtc tggcaagttt tagttaatat tagaaatgtg      5340
aagatgtcag cgggtttctg tccgctttct ctggagtttg tgtcggtgtg tattgtttat      5400
agaaataata taaaattagg tttgagagag aagattacaa acgtgagaga cggagggccc      5460
atggaactta cagaagaagt cgttgatgag ttcatggaag atgtccctat gtcgatcagg      5520
cttgcaaagt ttcgatctcg aaccggaaaa aagagtgatg tccgcaaagg gaaaaatagt      5580
agtagtgatc ggtcagtgcc gaacaagaac tatagaaatg ttaaggattt tggaggaatg      5640
agttttaaaa agaataattt aatcgatgat gattcggagg ctactgtcgc cgaatcggat      5700
tcgttttaaa tagatcttac agtatcacta ctccatctca gttcgtgttc ttgtcattaa      5760
ttaaatggct agcaaaggag aagaactttt cactggagtt gtcccaattc ttgttgaatt      5820
agatggtgat gttaatgggc acaaattttc tgtcagtgga gagggtgaag gtgatgctac      5880
atacggaaag cttacactta aatttatttg cactactgga aaactacctg ttccatggcc      5940
aacacttgtc actactttct cttatggtgt tcaatgcttt tcccgttatc cggatcatat      6000
gaaacggcat gactttttca agagtgccat gcccgaaggt tatgtacagg aacgcactat      6060
atctttcaaa gatgacggga actacaagac gcgtgctgaa gtcaagtttg aaggtgatac      6120
ccttgttaat cgtatcgagt taaaggtat tgattttaaa gaagatggaa acattctcgg      6180
acacaaactc gagtacaact ataactcaca caatgtatac atcacggcag acaaacaaaa      6240
gaatggaatc aaagctaact tcaaaattcg ccacaacatt gaagatggat ccgttcaact      6300
agcagaccat tatcaacaaa atactccaat tggcgatggc cctgtccttt taccagacaa      6360
ccattacctg tcgacacaat ctgccctttc gaaagatccc aacgaaaagc gtgaccacat      6420
ggtccttctt gagtttgtaa ctgctgctgg gattacacat ggcatggatg agctctacaa      6480
ataatgacac tcgagggta gtcaagatgc ataataaata acggattgtg tccgtaatca      6540
cacgtggtgc gtacgataac gcatagtgtt tttccctcca cttaaatcga agggttgtgt      6600
cttggatcgc gcgggtcaaa tgtatatggt tcatatacat ccgcaggcac gtaataaagc      6660
```

| | |
|---|---|
| gaggggttcg ggtcgaggtc ggctgtgaaa ctcgaaaagg ttccggaaaa caaaaaagag | 6720 |
| agtggtaggt aatagtgtta ataataagaa aataaataat agtggtaaga aaggtttgaa | 6780 |
| agttgaggaa attgaggata atgtaagtga tgacgagtct atcgcgtcat cgagtacgtt | 6840 |
| ttaatcaata tgccttatac aatcaactct ccgagccaat ttgtttactt aagttccgct | 6900 |
| tatgcagatc ctgtgcagct gatcaatctg tgtacaaatg cattgggtaa ccagtttcaa | 6960 |
| acgcaacaag ctaggacaac agtccaacag caatttgcgg atgcctggaa acctgtgcct | 7020 |
| agtatgacag tgagatttcc tgcatcggat ttctatgtgt atagatataa ttcgacgctt | 7080 |
| gatccgttga tcacggcgtt attaaatagc ttcgatacta gaaatagaat aatagaggtt | 7140 |
| gataatcaac ccgcaccgaa tactactgaa atcgttaacg cgactcagag ggtagacgat | 7200 |
| gcgactgtag ctataagggc ttcaatcaat aatttggcta atgaactggt tcgtggaact | 7260 |
| ggcatgttca atcaagcaag ctttgagact gctagtggac ttgtctggac cacaactccg | 7320 |
| gctacttagc tattgttgtg agatttccta aaataaagtc actgaagact taaaattcag | 7380 |
| ggtggctgat accaaaatca gcagtggttg ttcgtccact taaatataac gattgtcata | 7440 |
| tctggatcca acagttaaac catgtgatgg tgtatactgt ggtatggcgt aaaacaacgg | 7500 |
| aaaagtcgct gaagacttaa aattcagggt ggctgatacc aaaatcagca gtggttgttc | 7560 |
| gtccacttaa aaataacgat tgtcatatct ggatccaaca gttaaaccat gtgatggtgt | 7620 |
| atactgtggt atggcgtaaa acaacggaga ggttcgaatc ctcccctaac cgcgggtagc | 7680 |
| ggccca | 7686 |

<210> SEQ ID NO 3
<211> LENGTH: 807
<212> TYPE: DNA
<213> ORGANISM: Nicotiana tabacum

<400> SEQUENCE: 3

| | |
|---|---|
| atggctctag ttgttaaagg aaaagtgaat atcaatgagt ttatcgacct gacaaaaatg | 60 |
| gagaagatct taccgtcgat gtttacccct gtaaagagtg ttatgtgttc caagttgat | 120 |
| aaaataatgg ttcatgagaa tgagtcattg tcagggtga accttcttaa aggagttaag | 180 |
| cttattgata gtggatacgt ctgtttagcc ggtttggtcg tcacgggcga gtggaacttg | 240 |
| cctgacaatt gcagaggagg tgtgagcgtg tgtctggtgg acaaaaggat ggaaagagcc | 300 |
| gacgaggcca ctctcggatc ttactacaca gcagctgcaa agaaaagatt tcagttcaag | 360 |
| gtcgttccca attatgctat aaccacccag gacgcgatga aaacgtctg gcaagtttta | 420 |
| gttaatatta gaaatgtgaa gatgtcagcg ggtttctgtc cgctttctct ggagtttgtg | 480 |
| tcggtgtgta ttgtttatag aaataatata aaattaggtt tgagagagaa gattacaaac | 540 |
| gtgagagacg gagggcccat ggaacttaca gaagaagtcg ttgatgagtt catggaagat | 600 |
| gtccctatgt cgatcaggct tgcaaagttt cgatctcgaa ccggaaaaaa gagtgatgtc | 660 |
| cgcaaaggga aaaatagtag tagtgatcgg tcagtgccga acaagaacta tagaaatgtt | 720 |
| aaggattttg gaggaatgag ttttaaaaag aataatttaa tcgatgatga ttcggaggct | 780 |
| actgtcgccg aatcggattc gttttaa | 807 |

<210> SEQ ID NO 4
<211> LENGTH: 807
<212> TYPE: DNA
<213> ORGANISM: Nicotiana tabacum

```
<400> SEQUENCE: 4
atggctctag ttgttaaagg aaaagtgaat atcaatgagt ttatcgacct gacaaaaatg      60
gagaagatct taccgtcgat gtttacccct gtaaagagtg ttatgtgttc caaagttgat     120
aaaataatgg ttcatgagaa tgagtcattg tcagggatga accttcttaa aggagttaag     180
cttattgata gtggatacgt ctgtttagcc ggtttggtcg tcacgggcga gtggaacttg     240
cctgacaatt gcagaggagg tgtgagcgtg tgtctggtgg acaaaaggat ggaaagagcc     300
gacgaggcca ttctcggatc ttactacaca gcagctgcaa agaaaagatt tcagttcaag     360
gtcgttccca attatgctat aaccacccag gacgcgatga gaaacgtctg gcaagtttta     420
gttaatatta gaaatgtgaa gatgtcagcg ggtttctgtc cgctttctct ggagtttgtg     480
tcggtgtgta ttgtttatag aaataatata aaattaggtt tgagagagaa gattacaaac     540
gtgagagacg gagggcccat ggaacttaca gaagaagtcg ttgatgagtt catggaagat     600
gtccctatgt cgatcaggct tgcaaagttt cgatctcgaa ccggaaaaaa gagtgatgtc     660
cgcaaaggga aaaatagtag tagtgatcgg tcagtgccga acaagaacta tagaaatgtt     720
aaggattttg gaggaatgag ttttaaaaag aataatttaa tcgatgatga ttcggaggct     780
actgtcgccg aatcggattc gttttaa                                          807

<210> SEQ ID NO 5
<211> LENGTH: 268
<212> TYPE: PRT
<213> ORGANISM: Nicotiana tabacum

<400> SEQUENCE: 5

Met Ala Leu Val Val Lys Gly Lys Val Asn Ile Asn Glu Phe Ile Asp
  1               5                  10                  15

Leu Thr Lys Met Glu Lys Ile Leu Pro Ser Met Phe Thr Pro Val Lys
             20                  25                  30

Ser Val Met Cys Ser Lys Val Asp Lys Ile Met Val His Glu Asn Glu
         35                  40                  45

Ser Leu Ser Gly Val Asn Leu Leu Lys Gly Val Lys Leu Ile Asp Ser
     50                  55                  60

Gly Tyr Val Cys Leu Ala Gly Leu Val Val Thr Gly Glu Trp Asn Leu
 65                  70                  75                  80

Pro Asp Asn Cys Arg Gly Gly Val Ser Val Cys Leu Val Asp Lys Arg
                 85                  90                  95

Met Glu Arg Ala Asp Glu Ala Thr Leu Gly Ser Tyr Tyr Thr Ala Ala
            100                 105                 110

Ala Lys Lys Arg Phe Gln Phe Lys Val Val Pro Asn Tyr Ala Ile Thr
        115                 120                 125

Thr Gln Asp Ala Met Lys Asn Val Trp Gln Val Leu Val Asn Ile Arg
    130                 135                 140

Asn Val Lys Met Ser Ala Gly Phe Cys Pro Leu Ser Leu Glu Phe Val
145                 150                 155                 160

Ser Val Cys Ile Val Tyr Arg Asn Asn Ile Lys Leu Gly Leu Arg Glu
                165                 170                 175

Lys Ile Thr Asn Val Arg Asp Gly Gly Pro Met Glu Leu Thr Glu Glu
            180                 185                 190

Val Val Asp Glu Phe Met Glu Asp Val Pro Met Ser Ile Arg Leu Ala
        195                 200                 205

Lys Phe Arg Ser Arg Thr Gly Lys Lys Ser Asp Val Arg Lys Gly Lys
    210                 215                 220
```

-continued

```
Asn Ser Ser Ser Asp Arg Ser Val Pro Asn Lys Asn Tyr Arg Asn Val
225                 230                 235                 240

Lys Asp Phe Gly Gly Met Ser Phe Lys Lys Asn Asn Leu Ile Asp Asp
                245                 250                 255

Asp Ser Glu Ala Thr Val Ala Glu Ser Asp Ser Phe
            260                 265

<210> SEQ ID NO 6
<211> LENGTH: 268
<212> TYPE: PRT
<213> ORGANISM: Nicotiana tabacum

<400> SEQUENCE: 6

Met Ala Leu Val Val Lys Gly Lys Val Asn Ile Asn Glu Phe Ile Asp
1               5                   10                  15

Leu Thr Lys Met Glu Lys Ile Leu Pro Ser Met Glu Thr Pro Val Lys
                20                  25                  30

Ser Val Met Cys Ser Lys Val Asp Lys Ile Met Val His Glu Asn Glu
            35                  40                  45

Ser Leu Ser Gly Val Asn Leu Leu Lys Gly Val Lys Leu Ile Asp Ser
    50                  55                  60

Gly Tyr Val Cys Leu Ala Gly Leu Val Val Thr Gly Glu Trp Asn Leu
65                  70                  75                  80

Pro Asp Asn Cys Arg Gly Gly Val Ser Val Cys Leu Val Asp Lys Arg
                85                  90                  95

Met Glu Arg Ala Asp Glu Ala Ile Leu Gly Ser Tyr Tyr Thr Ala Ala
                100                 105                 110

Ala Lys Lys Arg Phe Gln Phe Lys Val Val Pro Asn Tyr Ala Ile Thr
            115                 120                 125

Thr Gln Asp Ala Met Arg Asn Val Trp Gln Val Leu Val Asn Ile Arg
            130                 135                 140

Asn Val Lys Met Ser Ala Gly Phe Cys Pro Leu Ser Leu Glu Phe Val
145                 150                 155                 160

Ser Val Cys Ile Val Tyr Arg Asn Asn Ile Lys Leu Gly Leu Arg Glu
                165                 170                 175

Lys Ile Thr Asn Val Arg Asp Gly Gly Pro Met Glu Leu Thr Glu Glu
            180                 185                 190

Val Val Asp Glu Phe Met Glu Asp Val Pro Met Ser Ile Arg Leu Ala
            195                 200                 205

Lys Phe Arg Ser Arg Thr Gly Lys Lys Ser Asp Val Arg Lys Gly Lys
    210                 215                 220

Asn Ser Ser Ser Asp Arg Ser Val Pro Asn Lys Asn Tyr Arg Asn Val
225                 230                 235                 240

Lys Asp Phe Gly Gly Met Ser Phe Lys Lys Asn Asn Leu Ile Asp Asp
                245                 250                 255

Asp Ser Glu Ala Thr Val Ala Glu Ser Asp Ser Phe
            260                 265
```